(12) United States Patent
Bolea et al.

(10) Patent No.: US 7,499,742 B2
(45) Date of Patent: Mar. 3, 2009

(54) ELECTRODE STRUCTURES AND METHODS FOR THEIR USE IN CARDIOVASCULAR REFLEX CONTROL

(75) Inventors: Stephen L. Bolea, Watertown, MN (US); Robert S. Kieval, Medina, MN (US); Bruce J. Persson, Albertville, MN (US); David J. Serdar, Shorewood, MN (US); Peter T. Keith, St. Paul, MN (US); Eric D. Irwin, Minneapolis, MN (US); Martin A. Rossing, Coon Rapids, MN (US)

(73) Assignee: CVRx, Inc., Minneapolis, MN (US)

( * ) Notice: Subject to any disclaimer, the term of this patent is extended or adjusted under 35 U.S.C. 154(b) by 514 days.

(21) Appl. No.: 10/402,911

(22) Filed: Mar. 27, 2003

(65) Prior Publication Data

US 2004/0010303 A1  Jan. 15, 2004

Related U.S. Application Data

(63) Continuation-in-part of application No. 09/963,777, filed on Sep. 26, 2001, now Pat. No. 7,158,832.

(60) Provisional application No. 60/368,222, filed on Mar. 27, 2002.

(51) Int. Cl.
*A61B 5/04* (2006.01)
*A61N 1/00* (2006.01)

(52) U.S. Cl. .............. 600/372; 607/2; 607/117

(58) Field of Classification Search ............ 607/118, 607/44, 117, 2, 6, 9; 128/784; 600/372, 600/373, 377, 381

See application file for complete search history.

(56) References Cited

U.S. PATENT DOCUMENTS

3,309,924 A * 3/1967 Kolin et al. .......... 73/861.12
3,522,811 A   8/1970 Schwartz et al.

(Continued)

FOREIGN PATENT DOCUMENTS

WO   WO 01/00273 A   1/2001

OTHER PUBLICATIONS

Brattstrom, A., Influence of Continuous and Intermittent (R-Wave Triggered) Electrical Stimulation of the Carotid Sinus Nerve on the Static Characteristic of the Circularoty Regulator:, Experientia 28:414-416, 1972.

(Continued)

*Primary Examiner*—George Manuel
*Assistant Examiner*—Christopher A Flory
(74) *Attorney, Agent, or Firm*—Townsend and Townsend and Crew LLP

(57) ABSTRACT

Devices, systems and methods are described by which the blood pressure, nervous system activity, and neurohormonal activity may be selectively and controllably reduced by activating baroreceptors. A baroreceptor activation device is positioned near a baroreceptor, preferably a baroreceptor located in the carotid sinus. A control system may be used to modulate the baroreceptor activation device. The control system may utilize an algorithm defining a stimulus regimen which promotes long term efficacy and reduces power requirements/consumption. The baroreceptor activation device may utilize electrodes to activate the baroreceptors. The electrodes may be adapted for connection to the carotid arteries at or near the carotid sinus, and may be designed to minimize extraneous tissue stimulation.

30 Claims, 15 Drawing Sheets

U.S. PATENT DOCUMENTS

| | | | |
|---|---|---|---|
| 3,650,277 A | 3/1972 | Sjostrand et al. | |
| 3,943,936 A | 3/1976 | Rasor et al. | |
| 4,323,073 A | 4/1982 | Ferris | |
| 4,573,481 A * | 3/1986 | Bullara | 607/118 |
| 4,590,946 A | 5/1986 | Loeb et al. | |
| 4,719,921 A | 1/1988 | Chirife | |
| 4,940,065 A * | 7/1990 | Tanagho et al. | 607/118 |
| 4,967,159 A | 10/1990 | Manes | |
| 5,040,533 A | 8/1991 | Feamot | |
| 5,199,428 A | 4/1993 | Obel et al. | |
| 5,215,089 A | 6/1993 | Baker, Jr. | |
| 5,282,468 A | 2/1994 | Klepinski | |
| 5,330,515 A | 7/1994 | Rutecki et al. | |
| 5,351,394 A | 10/1994 | Weinberg | |
| 5,411,540 A | 5/1995 | Edell et al. | |
| 5,540,734 A | 7/1996 | Zabara | |
| 5,540,735 A | 7/1996 | Wingrove | |
| 5,545,202 A | 8/1996 | Dahl et al. | |
| 5,571,150 A | 11/1996 | Wernicke et al. | |
| 5,643,330 A | 7/1997 | Holsheimer et al. | |
| 5,683,430 A | 11/1997 | Markowitz et al. | |
| 5,700,282 A | 12/1997 | Zabara | |
| 5,707,400 A | 1/1998 | Terry, Jr. et al. | |
| 5,727,558 A | 3/1998 | Hakki et al. | |
| 5,766,236 A | 6/1998 | Detty et al. | |
| 5,800,464 A | 9/1998 | Kieval et al. | |
| 5,861,015 A | 1/1999 | Benja-Athon | |
| 5,919,220 A | 7/1999 | Stieglitz et al. | |
| 5,938,596 A | 8/1999 | Woloszko et al. | |
| 5,989,230 A | 11/1999 | Frassica | |
| 6,006,134 A | 12/1999 | Hill et al. | |
| 6,016,449 A | 1/2000 | Fishell et al. | |
| 6,050,952 A | 4/2000 | Hakki et al. | |
| 6,073,048 A | 6/2000 | Kieval et al. | |
| 6,161,047 A * | 12/2000 | King et al. | 607/62 |
| 6,178,349 B1 | 1/2001 | Kieval | |
| 6,206,914 B1 | 3/2001 | Soykan | |
| 6,208,894 B1 | 3/2001 | Schulman et al. | |
| 6,292,703 B1 | 9/2001 | Meier et al. | |
| 6,397,109 B1 | 5/2002 | Cammilli et al. | |
| 6,401,129 B1 * | 6/2002 | Lenander | 709/238 |
| 6,438,428 B1 | 8/2002 | Axelgaard et al. | |
| 6,442,435 B2 * | 8/2002 | King et al. | 607/117 |
| 6,522,926 B1 | 2/2003 | Kieval et al. | |
| 6,564,101 B1 | 5/2003 | Zikria | |
| 6,894,204 B2 * | 5/2005 | Dunshee | 602/57 |
| 6,942,686 B1 * | 9/2005 | Barbut et al. | 607/105 |
| 7,010,337 B2 * | 3/2006 | Furnary et al. | 600/325 |
| 7,155,284 B1 | 12/2006 | Whitehurst et al. | |
| 2001/0023367 A1 * | 9/2001 | King et al. | 607/117 |
| 2002/0005982 A1 | 1/2002 | Borlinghaus | |
| 2002/0103516 A1 | 8/2002 | Patwardhan et al. | |
| 2002/0128700 A1 * | 9/2002 | Cross, Jr. | 607/117 |
| 2002/0151051 A1 | 10/2002 | Li | |
| 2003/0040785 A1 | 2/2003 | Maschino et al. | |

OTHER PUBLICATIONS

Peters et al., The Principle of Electrical Carotid Sinus Nerve Stimulation: A Nerve Pacemaker System for Angina Pectoris and Hypertension Therapy, Annals of Biomedical Engineering, 8:445-458, 1980.

Peters et al., Cardiovascular response to time delays of electrocardiogram-coupled electrical stimulation of carotid sinus nerves in dogs, Journal of the Autonomic Nervous Systems, 25:173-180, 1988.

Richter et al., The Course of Inhibition of Sympathetic Activity during Various Patterns of Carotid Sinus Nerve Stimulation, Pflugers Arch., 317:110-123, 1970.

Sedin, Gunnar, Responses of the Cardiovascular System to Carotid Sinus Nerve Stimulation, Upsala J Med Sci, 81:1-17, 1976.

Warzel et. al., Effects of carotis sinus nerve stimulation at different times in the respiratory and cardiac cycles on variability of heart rate and blood pressure of normotensive and renal hypertensive dogs, Journal of the Autonomic Nervous System, 26:121-127, 1989.

Warzel et. al., The Effect of Time of Electrical Stimulation of the Carotid Sinus on the Amount of Reduction in Arterial Pressure, Pflugers Arch., 337:39-44, 1972.

* cited by examiner

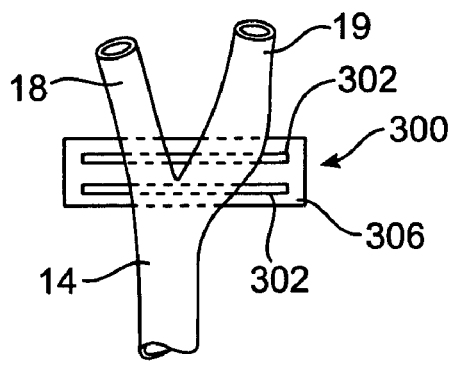
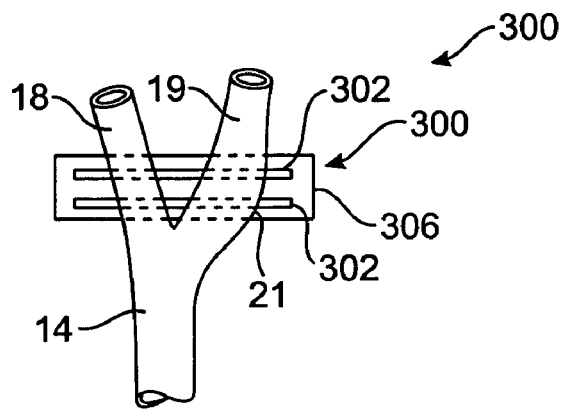
FIG. 5E    FIG. 5F
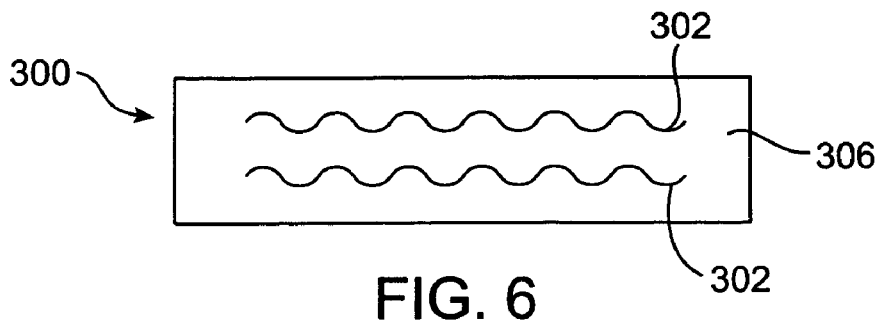
FIG. 6
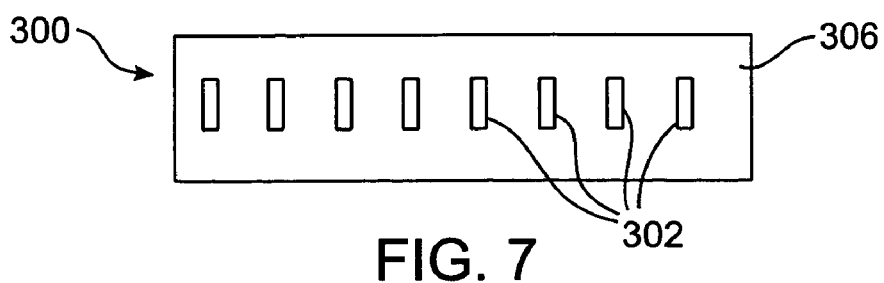
FIG. 7

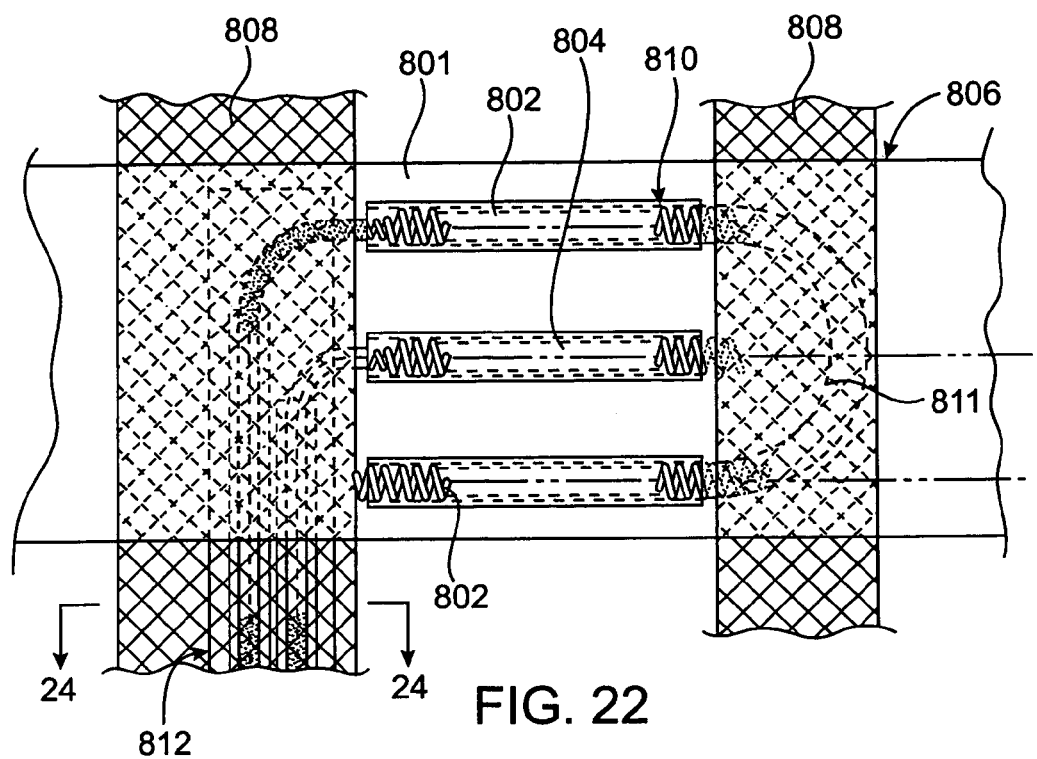
FIG. 22
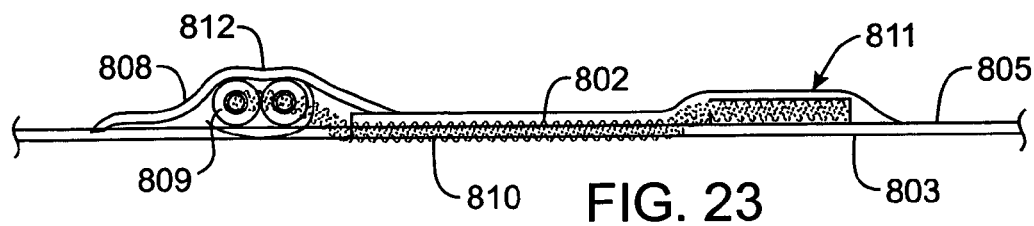
FIG. 23
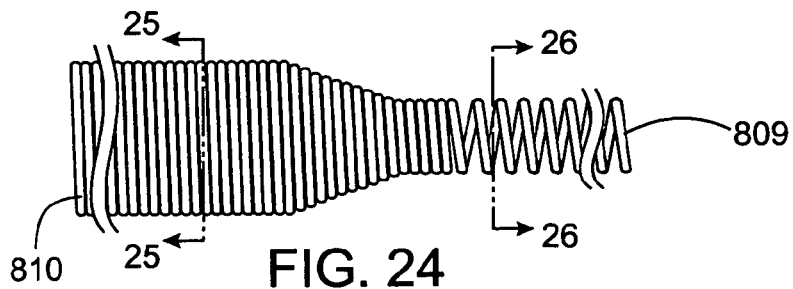
FIG. 24
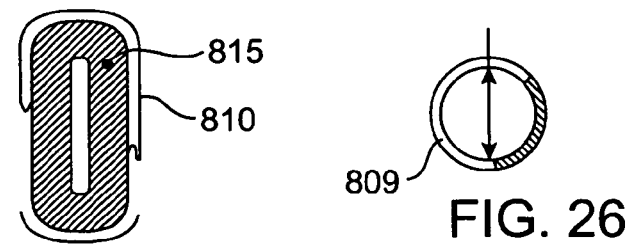
FIG. 25
FIG. 26

ELECTRODE STRUCTURES AND METHODS FOR THEIR USE IN CARDIOVASCULAR REFLEX CONTROL

CROSS-REFERENCES TO RELATED APPLICATIONS

This application claims the benefit of provisional application No. 60/368,222, filed on Mar. 27, 2002. This application is also a continuation-in-part of application Ser. No. 09/963,777), filed on Sep. 26, 2001. The full disclosures of each of these applications are incorporated herein by reference.

BACKGROUND OF THE INVENTION

FIELD OF THE INVENTION

The present invention generally relates to medical devices and methods of use for the treatment and/or management of cardiovascular and renal disorders. Specifically, the present invention relates to devices and methods for controlling the baroreflex system for the treatment and/or management of cardiovascular and renal disorders and their underlying causes and conditions.

Cardiovascular disease is a major contributor to patient illness and mortality. It also is a primary driver of health care expenditure, costing more than $326 billion each year in the United States. Hypertension, or high blood pressure, is a major cardiovascular disorder that is estimated to affect over 50 million people in the United Sates alone. Of those with hypertension, it is reported that fewer than 30% have their blood pressure under control. Hypertension is a leading cause of heart failure and stroke. It is the primary cause of death in over 42,000 patients per year and is listed as a primary or contributing cause of death in over 200,000 patients per year in the U.S. Accordingly, hypertension is a serious health problem demanding significant research and development for the treatment thereof.

Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year. It is also estimated that greater than 400,000 new cases of heart failure are diagnosed each year. Heart failure accounts for over 900,000 hospital admissions annually, and is the most common discharge diagnosis in patients over the age of 65 years. It has been reported that the cost of treating heart failure in the United States exceeds $20 billion annually. Accordingly, heart failure is also a serious health problem demanding significant research and development for the treatment and/or management thereof.

Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

A number of drug treatments have been proposed for the management of hypertension, heart failure and other cardiovascular disorders. These include vasodilators to reduce the blood pressure and ease the workload of the heart, diuretics to reduce fluid overload, inhibitors and blocking agents of the body's neurohormonal responses, and other medicaments.

Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month. Other surgical procedures are available as well.

It has been known for decades that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through activation of the sympathetic nervous system. Electrical stimulation of the carotid sinus nerve (baropacing) has previously been proposed to reduce blood pressure and the workload of the heart in the treatment of high blood pressure and angina. For example, U.S. Pat. No. 6,073,048 to Kieval et al. discloses a baroreflex modulation system and method for stimulating the baroreflex arc based on various cardiovascular and pulmonary parameters.

Although each of these alternative approaches is beneficial in some ways, each of the therapies has its own disadvantages. For example, drug therapy is often incompletely effective. Some patients may be unresponsive (refractory) to medical therapy. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease. Baropacing also has not gained acceptance. Several problems with electrical carotid sinus nerve stimulation have been reported in the medical literature. These include the invasiveness of the surgical procedure to implant the nerve electrodes, and postoperative pain in the jaw, throat, face and head during stimulation. In addition, it has been noted that high voltages sometimes required for nerve stimulation may damage the carotid sinus nerves. Accordingly, there continues to be a substantial and long felt need for new devices and methods for treating and/or managing high blood pressure, heart failure and their associated cardiovascular and nervous system disorders.

U.S. Pat. No. 6,522,926, signed to the Assignee of the present application, describes a number of systems and methods intended to activate baroreceptors in the carotid sinus and elsewhere in order to induce the baroreflex. Numerous specific approaches are described, including the use of coil electrodes placed over the exterior of the carotid sinus near the carotid bifurcation. While such electrode designs offer substantial promise, there is room for improvement in a number of specific design areas. For example, it would be desirable to provide designs which permit electrode structures to be closely and conformably secured over the exterior of a carotid sinus or other blood vessels so that efficient activation of the underlying baroreceptors can be achieved. It would be further desirable to provide specific electrode structures which can be variably positioned at different locations over the carotid sinus wall or elsewhere. At least some of these objectives will be met by these inventions described hereinbelow.

BRIEF SUMMARY OF THE INVENTION

To address hypertension, heart failure and their associated cardiovascular and nervous system disorders, the present invention provides a number of devices, systems and methods by which the blood pressure, nervous system activity, and neurohormonal activity may be selectively and controllably regulated by activating baroreceptors. By selectively and controllably activating baroreceptors, the present invention reduces excessive blood pressure, sympathetic nervous system activation and neurohormonal activation, thereby minimizing their deleterious effects on the heart, vasculature and other organs and tissues.

The present invention provides systems and methods for treating a patient by inducing a baroreceptor signal to effect a change in the baroreflex system (e.g., reduced heart rate, reduced blood pressure, etc.). The baroreceptor signal is activated or otherwise modified by selectively activating baroreceptors. To accomplish this, the system and method of the present invention utilize a baroreceptor activation device positioned near a baroreceptor in the carotid sinus, aortic arch, heart, common carotid arteries, subclavian arteries, and/or brachiocephalic artery. Preferably, the baroreceptor activation device is located in the right and/or left carotid sinus (near the bifurcation of the common carotid artery) and/or the aortic arch. By way of example, not limitation, the present invention is described with reference to the carotid sinus location.

Generally speaking, the baroreceptor activation device may be activated, deactivated or otherwise modulated to activate one or more baroreceptors and induce a baroreceptor signal or a change in the baroreceptor signal to thereby effect a change in the baroreflex system. The baroreceptor activation device may be activated, deactivated, or otherwise modulated continuously, periodically, or episodically. The baroreceptor activation device may comprise a wide variety of devices which utilize electrodes to directly or indirectly activate the baroreceptor. The baroreceptor may be activated directly, or activated indirectly via the adjacent vascular tissue. The baroreceptor activation device will be positioned outside the vascular wall. To maximize therapeutic efficacy, mapping methods may be employed to precisely locate or position the baroreceptor activation device.

The present invention is directed particularly at electrical means and methods to activate baroreceptors, and various electrode designs are provided. The electrode designs may be particularly suitable for connection to the carotid arteries at or near the carotid sinus, and may be designed to minimize extraneous tissue stimulation. While being particularly suitable for use on the carotid arteries at or near the carotid sinus, the electrode structures and assemblies of the present invention will also find use for external placement and securement of electrodes about other arteries, and in some cases veins, having baroreceptor and other electrically activated receptors therein.

In a first aspect of the present invention, a baroreceptor activation device or other electrode useful for a carotid sinus or other blood vessel comprises a base having one or more electrodes connected to the base. The base has a length sufficient to extend around at least a substantial portion of the circumference of a blood vessel, usually an artery, more usually a carotid artery at or near the carotid sinus. By "substantial portion," it is meant that the base will extend over at least 25% of the vessel circumference, usually at least 50%, more usually at least 66%, and often at least 75% or over the entire circumference. Usually, the base is sufficiently elastic to conform to said circumference or portion thereof when placed therearound. The electrode connected to the base is oriented at least partly in the circumferential direction and is sufficiently stretchable to both conform to the shape of the carotid sinus when the base is conformed thereover and accommodate changes in the shape and size of the sinus as they vary over time with heart pulse and other factors, including body movement which causes the blood vessel circumference to change.

Usually, at least two electrodes will be positioned circumferentially and adjacent to each other on the base. The electrode(s) may extend over the entire length of the base, but in some cases will extend over less than 75% of the circumferential length of the base, often being less than 50% of the circumferential length, and sometimes less than 25% of the circumferential length. Thus, the electrode structures may cover from a small portion up to the entire circumferential length of the carotid artery or other blood vessel. Usually, the circumferential length of the elongate electrodes will cover at least 10% of the circumference of the blood vessel, typically being at least 25%, often at least 50%, 75%, or the entire length. The base will usually have first and second ends, wherein the ends are adapted to be joined, and will have sufficient structural integrity to grasp the carotid sinus.

In a further aspect of the present invention, an extravascular electrode assembly comprises an elastic base and a stretchable electrode. The elastic base is adapted to be conformably attached over the outside of a target blood vessel, such as a carotid artery at or near the carotid sinus, and the stretchable electrode is secured over the elastic base and capable of expanding and contracting together with the base. In this way, the electrode assembly is conformable to the exterior of the carotid sinus or other blood vessel. Preferably, the elastic base is planar, typically comprising an elastomeric sheet. While the sheet may be reinforced, the reinforcement will be arranged so that the sheet remains elastic and stretchable, at least in the circumferential direction, so that the base and electrode assembly may be placed and conformed over the exterior of the blood vessel. Suitable elastomeric sheets may be composed of silicone, latex, and the like.

To assist in mounting the extravascular electrode over the carotid sinus or other blood vessel, the assembly will usually include two or more attachment tabs extending from the elastomeric sheet at locations which allow the tabs to overlap the elastic base and/or be directly attached to the blood vessel wall when the base is wrapped around or otherwise secured over a blood vessel. In this way, the tabs may be fastened to secure the backing over the blood vessel.

Preferred stretchable electrodes comprise elongated coils, where the coils may stretch and shorten in a spring-like manner. In particularly preferred embodiments, the elongated coils will be flattened over at least a portion of their lengths, where the flattened portion is oriented in parallel to the elastic base. The flattened coil provides improved electrical contact when placed against the exterior of the carotid sinus or other blood vessel.

In a further aspect of the present invention, an extravascular electrode assembly comprises a base and an electrode structure. The base is adapted to be attached over the outside of a carotid artery or other blood vessel and has an electrode-carrying surface formed over at least a portion thereof. A plurality of attachment tabs extend away from the electrode-carrying surface, where the tabs are arranged to permit selective ones thereof to be wrapped around a blood vessel while others of the tabs may be selectively removed. The electrode structure on or over the electrode-carrying surface.

In preferred embodiments, the base includes at least one tab which extends longitudinally from the electrode-carrying surface and at least two tabs which extend away from the surface at opposite, transverse angles. In an even more preferred embodiment, the electrode-carrying surface is rectangular, and at least two longitudinally extending tabs extend from adjacent corners of the rectangular surface. The two transversely angled tabs extend at a transverse angle away from the same two corners.

As with prior embodiments, the electrode structure preferably includes one or more stretchable electrodes secured to the electrode-carrying surface. The stretchable electrodes are preferably elongated coils, more preferably being "flattened coils" to enhance electrical contact with the blood vessel to be treated. The base is preferably an elastic base, more preferably being formed from an elastomeric sheet. The phrase "flattened coil," as used herein, refers to an elongate electrode structure including a plurality of successive turns where the cross-sectional profile is non-circular and which includes at least one generally flat or minimally curved face. Such coils may be formed by physically deforming (flattening) a circular coil, e.g., as shown in FIG. 24 described below. Usually, the flattened coils will have a cross-section that has a width in the plane of the electrode assembly greater than its height normal to the electrode assembly plane. Alternatively, the coils may be initially fabricated in the desired geometry having one generally flat (or minimally curved) face for contacting tissue. Fully flattened coils, e.g., those having planar serpentine configurations, may also find use, but usually it will be preferred to retain at least some thickness in the direction normal to the flat or minimally curved tissue-contacting surface. Such thickness helps the coiled electrode protrude from the base and provide improved tissue contact over the entire flattened surface.

In a still further aspect of the present invention, a method for wrapping an electrode assembly over a blood vessel comprises providing an electrode assembly having an elastic base and one or more stretchable electrodes. The base is conformed over an exterior of the blood vessel, such as a carotid artery, and at least a portion of an electrode is stretched along with the base. Ends of the elastic base are secured together to hold the electrode assembly in place, typically with both the elastic backing and stretchable electrode remaining under at least slight tension to promote conformance to the vessel exterior. The electrode assembly will be located over a target site in the blood vessel, typically a target site having an electrically activated receptor. Advantageously, the electrode structures of the present invention when wrapped under tension will flex and stretch with expansions and contractions of the blood vessel. A presently preferred target site is a baroreceptor, particularly baroreceptors in or near the carotid sinus.

In a still further aspect of the present invention, a method for wrapping an electrode assembly over a blood vessel comprises providing an electrode assembly including a base having an electrode-carrying surface and an electrode structure on the electrode-carrying surface. The base is wrapped over a blood vessel, and some but not all of a plurality of attachment tags on the base are secured over the blood vessel. Usually, the tabs which are not used to secure an electrode assembly will be removed, typically by cutting. Preferred target sites are electrically activated receptors, usually baroreceptors, more usually baroreceptors on the carotid sinus. The use of such electrode assemblies having multiple attachment tabs is particularly beneficial when securing the electrode assembly on a carotid artery near the carotid sinus. By using particular tabs, as described in more detail below, the active electrode area can be positioned at any of a variety of locations on the common, internal, and/or external carotid arteries.

In another aspect, the present invention comprises pressure measuring assemblies including an elastic base adapted to be mounted on the outer wall of a blood vessel under circumferential tension. A strain measurement sensor is positioned on the base to measure strain resulting from circumferential expansion of the vessel due to a blood pressure increase. Usually, the base will wrap about the entire circumference of the vessel, although only a portion of the base need be elastic. Alternatively, a smaller base may be stapled, glued, clipped or otherwise secured over a "patch" of the vessel wall to detect strain variations over the underlying surface. Exemplary sensors include strain gauges and micro machined sensors (MEMS).

In yet another aspect, electrode assemblies according to the present invention comprise a base and at least three parallel elongate electrode structures secured over a surface of the base. The base is attachable to an outside surface of a blood vessel, such as a carotid artery, particularly a carotid artery near the carotid sinus, and has a length sufficient to extend around at least a substantial portion of the circumference of the blood vessel, typically extending around at least 25% of the circumference, usually extending around at least 50% of the circumference, preferably extending at least 66% of the circumference, and often extending around at least 75% of or the entire circumference of the blood vessel. As with prior embodiments, the base will preferably be elastic and composed of any of the materials set forth previously.

The at least three parallel elongate electrode structures will preferably be aligned in the circumferential direction of the base, i.e., the axis or direction of the base which will be aligned circumferentially over the blood vessel when the base is mounted on the blood vessel. The electrode structures will preferably be stretchable, typically being elongate coils, often being flattened elongate coils, as also described previously.

At least an outer pair of the electrode structures will be electrically isolated from an inner electrode structure, and the outer electrode structures will preferably be arranged in a U-pattern in order to surround the inner electrode structure. In this way, the outer pair of electrodes can be connected using a single conductor taken from the base, and the outer electrode structures and inner electrode structure may be connected to separate poles on a power supply in order to operate in the "pseudo" tripolar mode described hereinbelow.

To address low blood pressure and other conditions requiring blood pressure augmentation, the present invention provides electrode designs and methods utilizing such electrodes by which the blood pressure may be selectively and controllably regulated by inhibiting or dampening baroreceptor signals. By selectively and controllably inhibiting or dampening baroreceptor signals, the present invention reduces conditions associated with low blood pressure.

BRIEF DESCRIPTION OF THE DRAWINGS

FIGS. 5A-5F are schematic illustrations of various possible arrangements of electrodes around the carotid sinus for extravascular electrical activation embodiments.

FIG. 6 is a schematic illustration of a serpentine shaped electrode for extravascular electrical activation embodiments.

FIG. 7 is a schematic illustration of a plurality of electrodes aligned orthogonal to the direction of wrapping around the carotid sinus for extravascular electrical activation embodiments.

FIG. 22 is a detailed view of the electrode-carrying surface of an electrode assembly similar to that shown in FIG. 20, except that the electrodes have been flattened.

FIG. 23 is a cross-sectional view of the electrode structure of FIG. 22.

FIG. 24 illustrates the transition between the flattened and non-flattened regions of the electrode coil of the electrode assembly FIG. 20.

FIG. 25 is a cross-sectional view taken along the line 25-25 of FIG. 24.

FIG. 26 is a cross-sectional view taken along the line 26-26 of FIG. 24.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
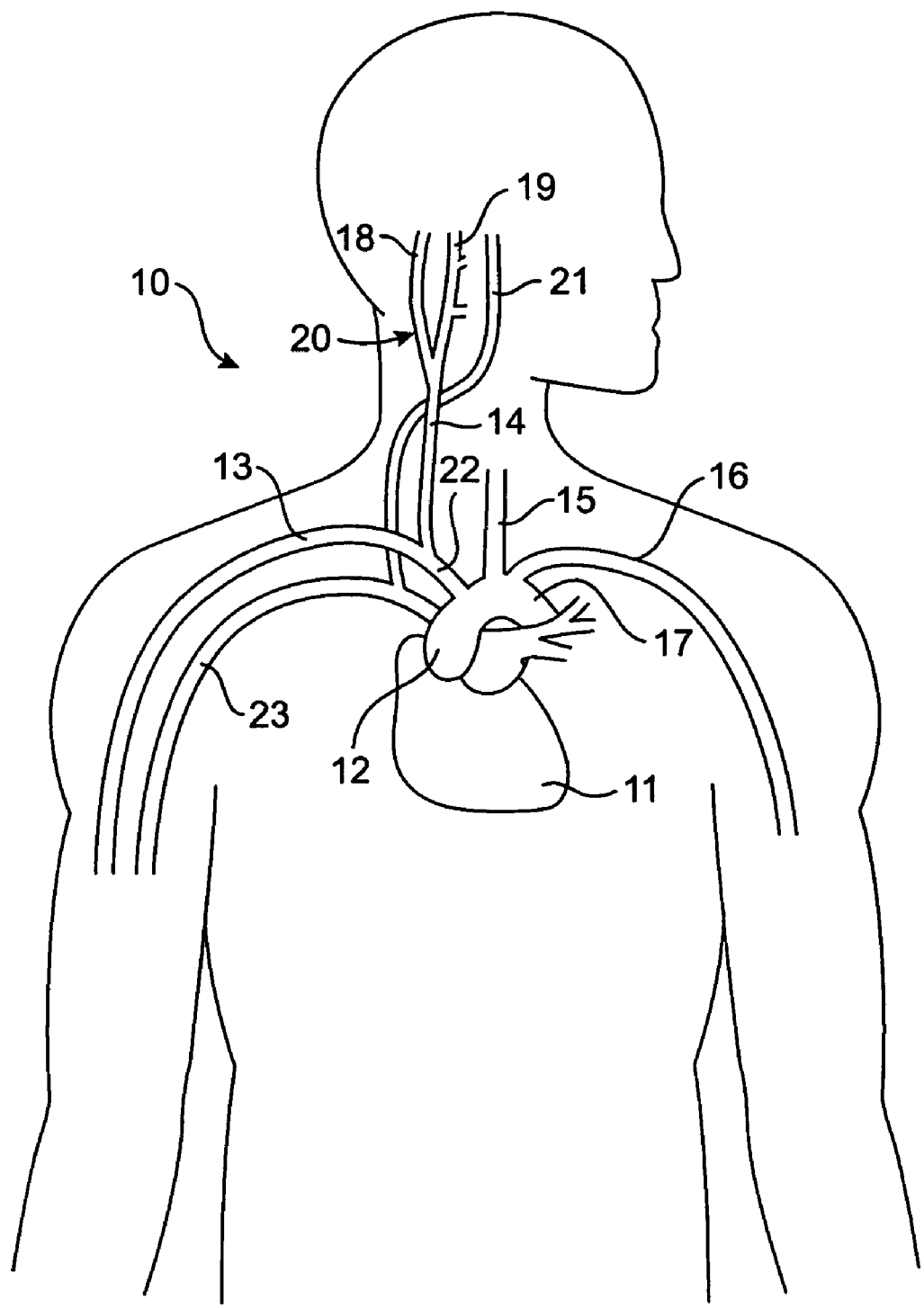
FIG. 1 is a schematic illustration of the upper torso of a human body showing the major arteries and veins and associated anatomy.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the sub clavian arteries 13/16, oxygenated blood circulates through the upper peripheral vasculature and oxygen depleted blood returns to the heart by way of the subclavian veins, of which only the right subclavian vein 23 is shown, also for sake of clarity. The heart 11 pumps the oxygen depleted blood through the pulmonary system where it is reoxygenated. The re-oxygenated blood returns to the heart 11 which pumps the re-oxygenated blood into the aortic arch as described above, and the cycle repeats.

Figures 2A, 2B:
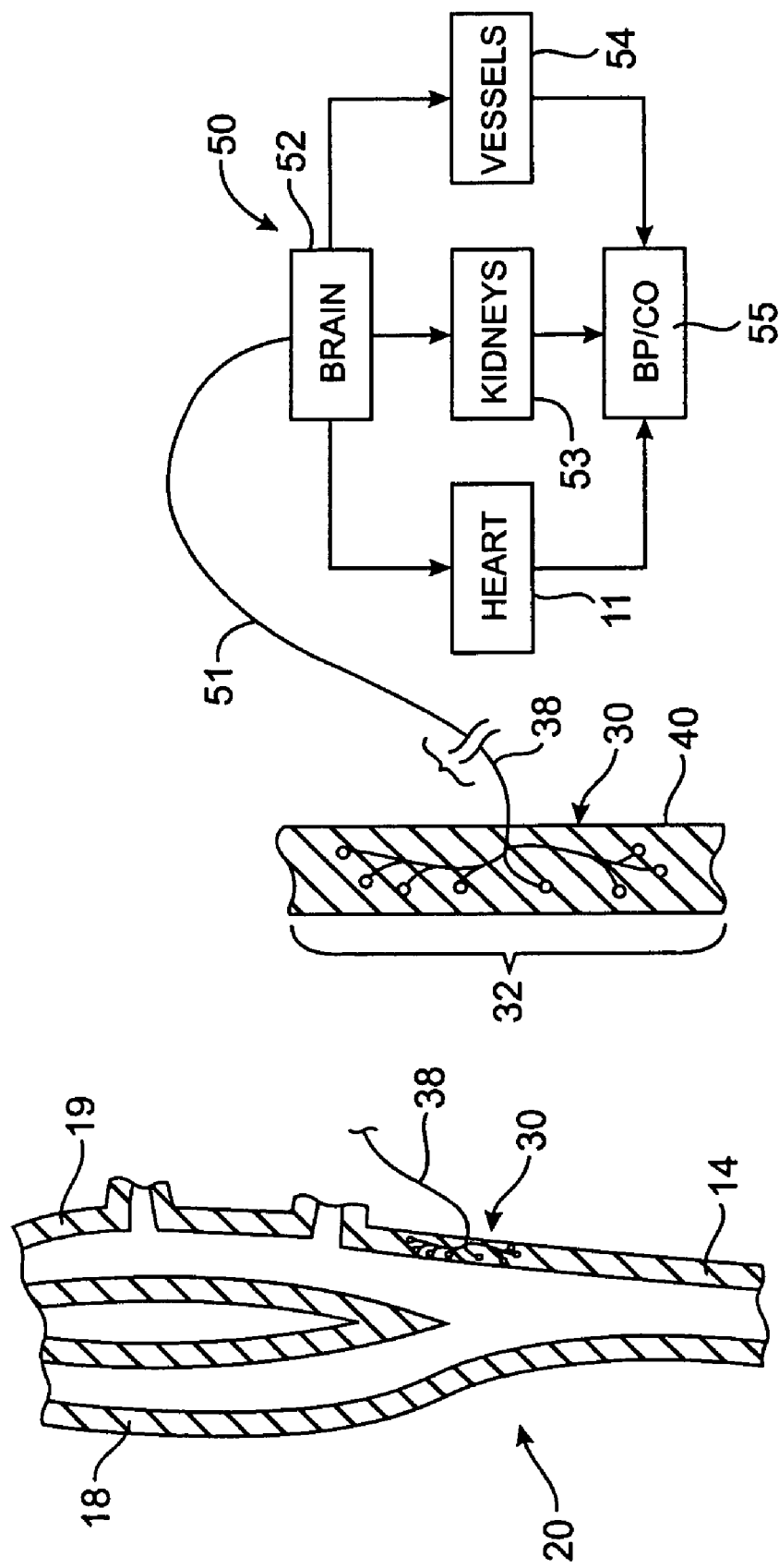
FIG. 2A is a cross-sectional schematic illustration of the carotid sinus and baroreceptors within the vascular wall.
FIG. 2B is a schematic illustration of baroreceptors within the vascular wall and the baroreflex system.

Within the arterial walls of the aortic arch 12, common carotid arteries 14/15 (near the right carotid sinus 20 and left carotid sinus), subclavian arteries 13/16 and brachiocephalic artery 22 there are baroreceptors 30. For example, as best seen in FIG. 2A, baroreceptors 30 reside within the vascular walls of the carotid sinus 20. Baroreceptors 30 are a type of stretch receptor used by the body to sense blood pressure. An increase in blood pressure causes the arterial wall to stretch, and a decrease in blood pressure causes the arterial wall to return to its original size. Such a cycle is repeated with each beat of the heart. Because baroreceptors 30 are located within the arterial wall, they are able to sense deformation of the adjacent tissue, which is indicative of a change in blood pressure. The baroreceptors 30 located in the right carotid sinus 20, the left carotid sinus and the aortic arch 12 play the most significant role in sensing blood pressure that affects the baroreflex system 50, which is described in more detail with reference to FIG. 2B.

Refer now to FIG. 2B, which shows a schematic illustration of baroreceptors 30 disposed in a generic vascular wall 40 and a schematic flow chart of the baroreflex system 50. Baroreceptors 30 are profusely distributed within the arterial walls 40 of the major arteries discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, those skilled in the art will appreciate that the baroreceptors 30 shown in FIG. 2B are primarily schematic for purposes of illustration and discussion.

Baroreceptor signals are used to activate a number of body systems which collectively may be referred to as the baroreflex system 50. Baroreceptors 30 are connected to the brain 52 via the nervous system 51. Thus, the brain 52 is able to detect changes in blood pressure, which is indicative of cardiac output. If cardiac output is insufficient to meet demand (i.e., the heart 11 is unable to pump sufficient blood), the baroreflex system 50 activates a number of body systems, including the heart 11, kidneys 53, vessels 54, and other organs/tissues. Such activation of the baroreflex system 50 generally corresponds to an increase in neurohormonal activity. Specifically, the baroreflex system 50 initiates a neurohormonal sequence that signals the heart 11 to increase heart rate and increase contraction force in order to increase cardiac output, signals the kidneys 53 to increase blood volume by retaining sodium and water, and signals the vessels 54 to constrict to elevate blood pressure. The cardiac, renal and vascular responses increase blood pressure and cardiac output 55, and thus increase the workload of the heart 11. In a patient with heart failure, this further accelerates myocardial damage and exacerbates the heart failure state.

To address the problems of hypertension, heart failure, other cardiovascular disorders and renal disorders, the present invention basically provides a number of devices, systems and methods by which the baroreflex system 50 is activated to reduce excessive blood pressure, autonomic nervous system activity and neurohormonal activation. In particular, the present invention provides a number of devices, systems and methods by which baroreceptors 30 may be activated, thereby indicating an increase in blood pressure and signaling the brain 52 to reduce the body's blood pressure and level of sympathetic nervous system and neurohormonal activation, and increase parasypathetic nervous system activation, thus having a beneficial effect on the cardiovascular system and other body systems.

Figure 3:
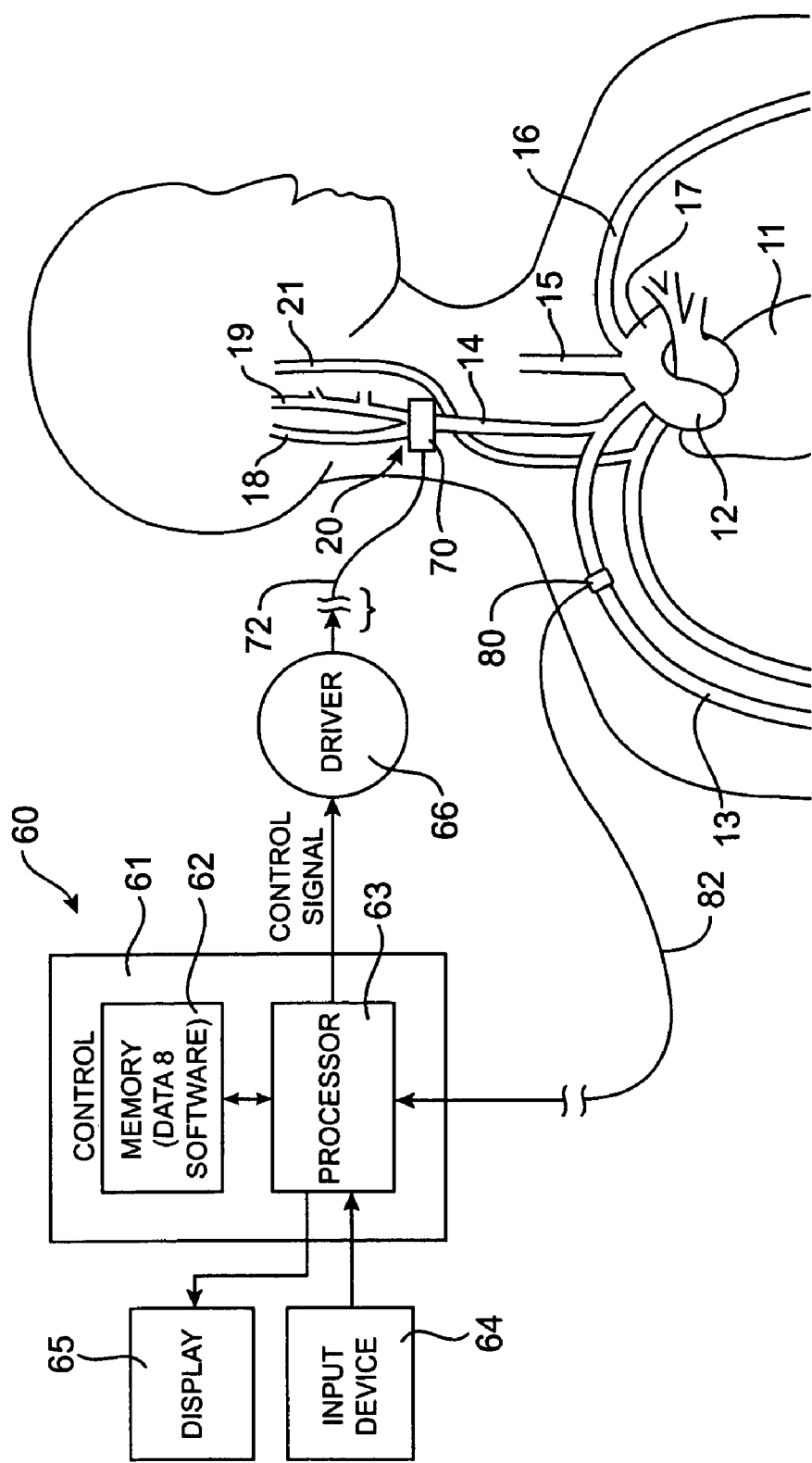
FIG. 3 is a schematic illustration of a baroreceptor activation system in accordance with the present invention.

With reference to FIG. 3, the present invention generally provides a system including a control system 60, a baroreceptor activation device 70, and a sensor 80 (optional), which generally operate in the following manner. The sensor(s) 80 optionally senses and/or monitors a parameter (e.g., cardiovascular function) indicative of the need to modify the baroreflex system and generates a signal indicative of the parameter.

The control system 60 generates a control signal as a function of the received sensor signal. The control signal activates, deactivates or otherwise modulates the baroreceptor activation device 70. Typically, activation of the device 70 results in activation of the baroreceptors 30. Alternatively, deactivation or modulation of the baroreceptor activation device 70 may cause or modify activation of the baroreceptors 30. The baroreceptor activation device 70 may comprise a wide variety of devices which utilize electrical means to activate baroreceptors 30. Thus, when the sensor 80 detects a parameter indicative of the need to modify the baroreflex system activity (e.g., excessive blood pressure), the control system 60 generates a control signal to modulate (e.g. activate) the baroreceptor activation device 70 thereby inducing a baroreceptor 30 signal that is perceived by the brain 52 to be apparent excessive blood pressure. When the sensor 80 detects a parameter indicative of normal body function (e.g., normal blood pressure), the control system 60 generates a control signal to modulate (e.g., deactivate) the baroreceptor activation device 70.

As mentioned previously, the baroreceptor activation device 70 may comprise a wide variety of devices which utilize electrical means to activate the baroreceptors 30. The baroreceptor activation device 70 of the present invention comprises an electrode structure which directly activates one or more baroreceptors 30 by changing the electrical potential across the baroreceptors 30. It is possible that changing the electrical potential across the tissue surrounding the baroreceptors 30 may cause the surrounding tissue to stretch or otherwise deform, thus mechanically activating the baroreceptors 30, in which case the stretchable and elastic electrode structures of the present invention may provide significant advantages.

All of the specific embodiments of the electrode structures of the present invention are suitable for implantation, and are preferably implanted using a minimally invasive surgical approach. The baroreceptor activation device 70 may be positioned anywhere baroreceptors 30 are present. Such potential implantation sites are numerous, such as the aortic arch 12, in the common carotid arteries 18/19 near the carotid sinus 20, in the subclavian arteries 13/16, in the brachiocephalic artery 22, or in other arterial or venous locations. The electrode structures of the present invention will be implanted such that they are positioned on or over a vascular structure immediately adjacent the baroreceptors 30. Preferably, the electrode structure of the baroreceptor activation device 70 is implanted near the right carotid sinus 20 and/or the left carotid sinus (near the bifurcation of the common carotid artery) and/or the aortic arch 12, where baroreceptors 30 have a significant impact on the baroreflex system 50. For purposes of illustration only, the present invention is described with reference to baroreceptor activation device 70 positioned near the carotid sinus 20.

The optional sensor 80 is operably coupled to the control system 60 by electric sensor cable or lead 82. The sensor 80 may comprise any suitable device that measures or monitors a parameter indicative of the need to modify the activity of the baroreflex system. For example, the sensor 80 may comprise a physiologic transducer or gauge that measures ECG, blood pressure (systolic, diastolic, average or pulse pressure), blood volumetric flow rate, blood flow velocity, blood pH, O2 or CO2 content, mixed venous oxygen saturation (SVO2), vasoactivity, nerve activity, tissue activity, body movement, activity levels, respiration, or composition. Examples of suitable transducers or gauges for the sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector (SVO2), tissue impedance (electrical), or a strain gauge. Although only one sensor 80 is shown, multiple sensors 80 of the same or different type at the same or different locations may be utilized.

An example of an implantable blood pressure measurement device that may be disposed about a blood vessel is disclosed in U.S. Pat. No. 6,106,477 to Miesel et al., the entire disclosure of which is incorporated herein by reference. An example of a subcutaneous ECG monitor is available from Medtronic under the trade name REVEAL ILR and is disclosed in PCT Publication No. WO 98/02209, the entire disclosure of which is incorporated herein by reference. Other examples are disclosed in U.S. Pat. Nos. 5,987,352 and 5,331,966, the entire disclosures of which are incorporated herein by reference. Examples of devices and methods for measuring absolute blood pressure utilizing an ambient pressure reference are disclosed in U.S. Pat. No. 5,810,735 to Halperin et al., U.S. Pat. No. 5,904,708 to Goedeke, and PCT Publication No. WO 00/16686 to Brockway et al., the entire disclosures of which are incorporated herein by reference. The sensor 80 described herein may take the form of any of these devices or other devices that generally serve the same purpose.

The sensor 80 is preferably positioned in a chamber of the heart 11, or in/on a major artery such as the aortic arch 12, a common carotid artery 14/15, a subclavian artery 13/16 or the brachiocephalic artery 22, such that the parameter of interest may be readily ascertained. The sensor 80 may be disposed inside the body such as in or on an artery, a vein or a nerve (e.g. vagus nerve), or disposed outside the body, depending on the type of transducer or gauge utilized. The sensor 80 may be separate from the baroreceptor activation device 70 or combined therewith. For purposes of illustration only, the sensor 80 is shown positioned on the right subclavian artery 13.

By way of example, the control system 60 includes a control block 61 comprising a processor 63 and a memory 62. Control system 60 is connected to the sensor 80 by way of sensor cable 82. Control system 60 is also connected to the baroreceptor activation device 70 by way of electric control cable 72. Thus, the control system 60 receives a sensor signal from the sensor 80 by way of sensor cable 82, and transmits a control signal to the baroreceptor activation device 70 by way of control cable 72.

The system components 60/70/80 may be directly linked via cables 72/82 or by indirect means such as RF signal transceivers, ultrasonic transceivers or galvanic couplings. Examples of such indirect interconnection devices are disclosed in U.S. Pat. No. 4,987,897 to Funke and U.S. Pat. No. 5,113,859 to Funke, the entire disclosures of which are incorporated herein by reference.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event. The algorithm may dynamically alter the threshold value as determined by the sensor input values.

As mentioned previously, the baroreceptor activation device 70 activates baroreceptors 30 electrically, optionally in combination with mechanical, thermal, chemical, biological or other co-activation. In some instances, the control system 60 includes a driver 66 to provide the desired power mode for the baroreceptor activation device 70. For example, the driver 66 may comprise a power amplifier or the like and the cable 72 may comprise electrical lead(s). In other instances, the driver 66 may not be necessary, particularly if the processor 63 generates a sufficiently strong electrical signal for low level electrical actuation of the baroreceptor activation device 70.

The control system 60 may operate as a closed loop utilizing feedback from the sensor 80, or other sensors, such as heart rate sensors which may be incorporated or the electrode assembly, or as an open loop utilizing reprogramming commands received by input device 64. The closed loop operation of the control system 60 preferably utilizes some feedback from the transducer 80, but may also operate in an open loop mode without feedback. Programming commands received by the input device 64 may directly influence the control signal, the output activation parameters, or may alter the software and related algorithms contained in memory 62. The treating physician and/or patient may provide commands to input device 64. Display 65 may be used to view the sensor signal, control signal and/or the software/data contained in memory 62.

The control signal generated by the control system 60 may be continuous, periodic, alternating, episodic or a combination thereof, as dictated by an algorithm contained in memory 62. Continuous control signals include a constant pulse, a constant train of pulses, a triggered pulse and a triggered train of pulses. Examples of periodic control signals include each of the continuous control signals described above which have a designated start time (e.g., beginning of each period as designated by minutes, hours, or days in combinations of) and a designated duration (e.g., seconds, minutes, hours, or days in combinations of). Examples of alternating control signals include each of the continuous control signals as described above which alternate between the right and left output channels. Examples of episodic control signals include each of the continuous control signals described above which are triggered by an episode (e.g., activation by the physician/patient, an increase/decrease in blood pressure above a certain threshold, heart rate above/below certain levels, etc.).

The stimulus regimen governed by the control system 60 may be selected to promote long term efficacy. It is theorized that uninterrupted or otherwise unchanging activation of the baroreceptors 30 may result in the baroreceptors and/or the baroreflex system becoming less responsive over time, thereby diminishing the long term effectiveness of the therapy. Therefore, the stimulus regimen maybe selected to activate, deactivate or otherwise modulate the baroreceptor activation device 70 in such a way that therapeutic efficacy is maintained preferably for years.

In addition to maintaining therapeutic efficacy over time, the stimulus regimens of the present invention may be selected reduce power requirement/consumption of the system 60. As will be described in more detail hereinafter, the stimulus regimen may dictate that the baroreceptor activation device 70 be initially activated at a relatively higher energy and/or power level, and subsequently activated at a relatively lower energy and/or power level. The first level attains the desired initial therapeutic effect, and the second (lower) level sustains the desired therapeutic effect long term. By reducing the energy and/or power levels after the desired therapeutic effect is initially attained, the energy required or consumed by the activation device 70 is also reduced long term. This may correlate into systems having greater longevity and/or reduced size (due to reductions in the size of the power supply and associated components).

A first general approach for a stimulus regimen which promotes long term efficacy and reduces power requirements/consumption involves generating a control signal to cause the baroreceptor activation device 70 to have a first output level of relatively higher energy and/or power, and subsequently changing the control signal to cause the baroreceptor activation device 70 to have a second output level of relatively lower energy and/or power. The first output level may be selected and maintained for sufficient time to attain the desired initial effect (e.g., reduced heart rate and/or blood pressure), after which the output level may be reduced to the second level for sufficient time to sustain the desired effect for the desired period of time.

For example, if the first output level has a power and/or energy value of X1, the second output level may have a power and/or energy value of X2, wherein X2 is less than X1. In some instances, X2 may be equal to zero, such that the first level is "on" and the second level is "off". It is recognized that power and energy refer to two different parameters, and in some cases, a change in one of the parameters (power or energy) may not correlate to the same or similar change in the other parameter. In the present invention, it is contemplated that a change in one or both of the parameters may be suitable to obtain the desired result of promoting long term efficacy.

It is also contemplated that more than two levels may be used. Each further level may increase the output energy or power to attain the desired effect, or decrease the output energy or power to retain the desired effect. For example, in some instances, it may be desirable to have further reductions in the output level if the desired effect may be sustained at lower power or energy levels. In other instances, particularly when the desired effect is diminishing or is otherwise not sustained, it may be desirable to increase the output level until the desired effect is reestablished, and subsequently decrease the output level to sustain the effect.

The transition from each level may be a step function (e.g., a single step or a series of steps), a gradual transition over a period of time, or a combination thereof. In addition, the signal levels may be continuous, periodic, alternating, or episodic as discussed previously.

In electrical activation using a non modulated signal, the output (power or energy) level of the baroreceptor activation device 70 may be changed by adjusting the output signal voltage level, current level and/or signal duration. The output signal of the baroreceptor activation device 70 may be, for example, constant current or constant voltage. In electrical activation embodiments using a modulated signal, wherein the output signal comprises, for example, a series of pulses, several pulse characteristics may be changed individually or in combination to change the power or energy level of the output signal. Such pulse characteristics include, but are not limited to: pulse amplitude (PA), pulse frequency (PF), pulse width or duration (PW), pulse waveform (square, triangular, sinusoidal, etc.), pulse polarity (for bipolar electrodes) and pulse phase (monophasic, biphasic).

In electrical activation wherein the output signal comprises a pulse train, several other signal characteristics may be changed in addition to the pulse characteristics described above, as described in copending application Ser. No. 09/964,079, the full disclosure of which is incorporated herein by reference.

Figure 4B:
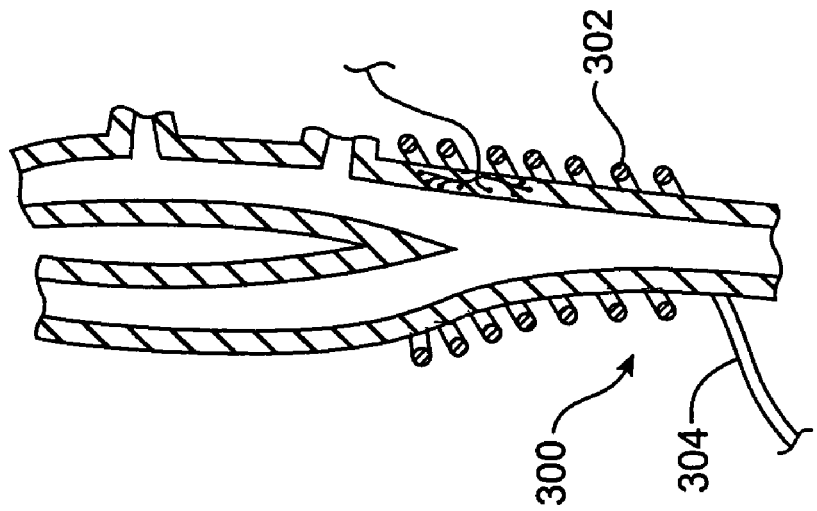
FIGS. 4A and 4B are schematic illustrations of a baroreceptor activation device in the form of an implantable extraluminal conductive structure which electrically induces a baroreceptor signal in accordance with an embodiment of the present invention.
Figure 4A:
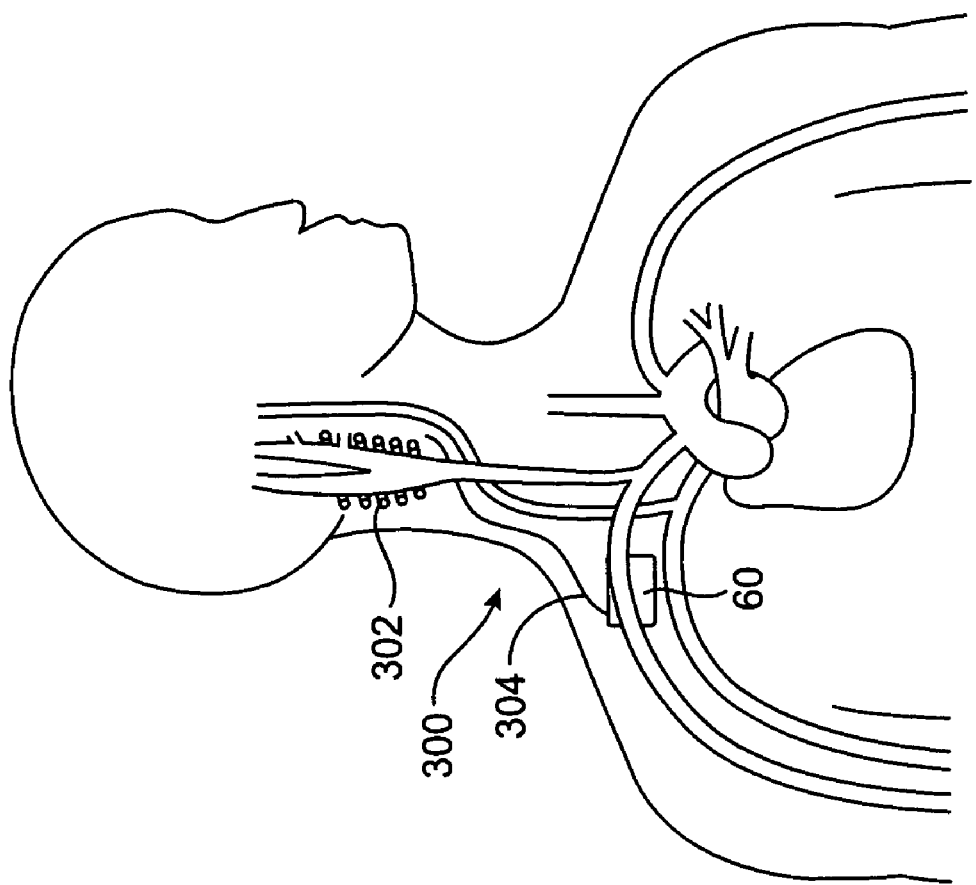

FIGS. 4A and 4B show schematic illustrations of a baroreceptor activation device 300 in the form of an extravascular electrically conductive structure or electrode 302. The electrode structure 302 may comprise a coil, braid or other structure capable of surrounding the vascular wall. Alternatively, the electrode structure 302 may comprise one or more electrode patches distributed around the outside surface of the vascular wall. Because the electrode structure 302 is disposed on the outside surface of the vascular wall, intravascular delivery techniques may not be practical, but minimally invasive surgical techniques will suffice. The extravascular electrode structure 302 may receive electrical signals directly from the driver 66 of the control system 60 by way of electrical lead 304, or indirectly by utilizing an inductor (not shown) as described in copending commonly assigned application Ser. No. 10/402,393, filed on the same day as the present application, the full disclosure of which is incorporated herein by reference.

Refer now to FIGS. 5A-5F which show schematic illustrations of various possible arrangements of electrodes around the carotid sinus 20 for extravascular electrical activation embodiments, such as baroreceptor activation device 300 described with reference to FIGS. 4A and 4B. The electrode designs illustrated and described hereinafter may be particularly suitable for connection to the carotid arteries at or near the carotid sinus, and may be designed to minimize extraneous tissue stimulation.

In FIGS. 5A-5F, the carotid arteries are shown, including the common 14, the external 18 and the internal 19 carotid arteries. The location of the carotid sinus 20 may be identified by a landmark bulge 21, which is typically located on the internal carotid artery 19 just distal of the bifurcation, or extends across the bifurcation from the common carotid artery 14 to the internal carotid artery 19.

The carotid sinus 20, and in particular the bulge 21 of the carotid sinus, may contain a relatively high density of baroreceptors 30 (not shown) in the vascular wall. For this reason, it may be desirable to position the electrodes 302 of the activation device 300 on and/or around the sinus bulge 21 to maximize baroreceptor responsiveness and to minimize extraneous tissue stimulation.

It should be understood that the device 300 and electrodes 302 are merely schematic, and only a portion of which may be shown, for purposes of illustrating various positions of the electrodes 302 on and/or around the carotid sinus 20 and the sinus bulge 21. In each of the embodiments described herein, the electrodes 302 may be monopolar, bipolar, or tripolar (anode-cathode-anode or cathode-anode-cathode sets). Specific extravascular electrode designs are described in more detail hereinafter.

Figure 5A:
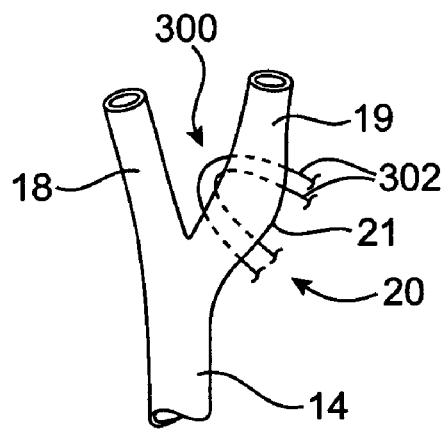
Figure 5B:
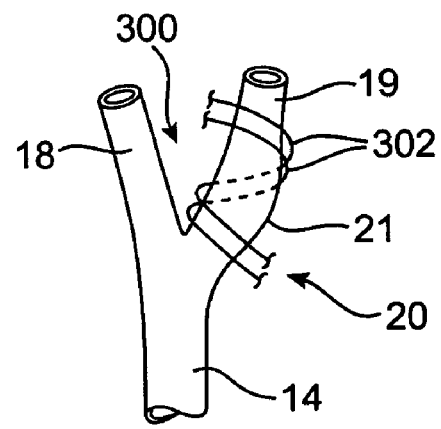
Figure 5C:
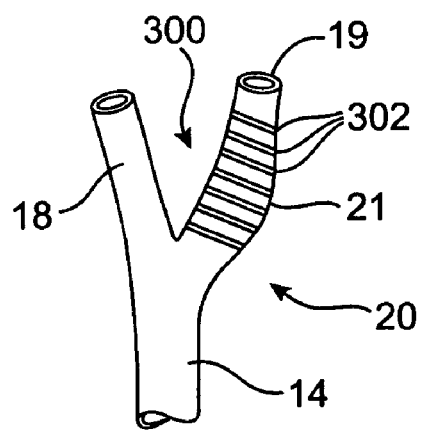

In FIG. 5A, the electrodes 302 of the extravascular electrical activation device 300 extend around a portion or the entire circumference of the sinus 20 in a circular fashion. Often, it would be desirable to reverse the illustrated electrode configuration in actual use. In FIG. 5B, the electrodes 302 of the extravascular electrical activation device 300 extend around a portion or the entire circumference of the sinus 20 in a helical fashion. In the helical arrangement shown in FIG. 5B, the electrodes 302 may wrap around the sinus 20 any number of times to establish the desired electrode 302 contact and coverage. In the circular arrangement shown in FIG. 5A, a single pair of electrodes 302 may wrap around the sinus 20, or a plurality of electrode pairs 302 may be wrapped around the sinus 20 as shown in FIG. 5C to establish more electrode 302 contact and coverage.

The plurality of electrode pairs 302 may extend from a point proximal of the sinus 20 or bulge 21, to a point distal of the sinus 20 or bulge 21 to ensure activation of baroreceptors 30 throughout the sinus 20 region. The electrodes 302 may be connected to a single channel or multiple channels as discussed in more detail hereinafter. The plurality of electrode pairs 302 may be selectively activated for purposes of targeting a specific area of the sinus 20 to increase baroreceptor responsiveness, or for purposes of reducing the exposure of tissue areas to activation to maintain baroreceptor responsiveness long term.

Figure 5D:
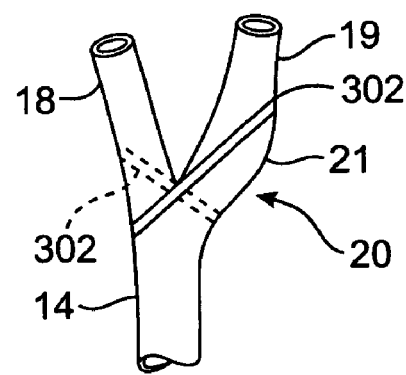

In FIG. 5D, the electrodes 302 extend around the entire circumference of the sinus 20 in a criss cross fashion. The criss cross arrangement of the electrodes 302 establishes contact with both the internal 19 and external 18 carotid arteries around the carotid sinus 20. Similarly, in FIG. 5E, the electrodes 302 extend around all or a portion of the circumference of the sinus 20, including the internal 19 and external 18 carotid arteries at the bifurcation, and in some instances the common carotid artery 14. In FIG. 5F, the electrodes 302 extend around all or a portion of the circumference of the sinus 20, including the internal 19 and external 18 carotid arteries distal of the bifurcation. In FIGS. 5E and 5F, the extravascular electrical activation devices 300 are shown to include a substrate or base structure 306 which may encapsulate and insulate the electrodes 302 and may provide a means for attachment to the sinus 20 as described in more detail hereinafter.

From the foregoing discussion with reference to FIGS. 5A-5F, it should be apparent that there are a number of suitable arrangements for the electrodes 302 of the activation device 300, relative to the carotid sinus 20 and associated anatomy. In each of the examples given above, the electrodes 302 are wrapped around a portion of the carotid structure, which may require deformation of the electrodes 302 from their relaxed geometry (e.g., straight). To reduce or eliminate such deformation, the electrodes 302 and/or the base structure 306 may have a relaxed geometry that substantially conforms to the shape of the carotid anatomy at the point of attachment. In other words, the electrodes 302 and the base structure or backing 306 may be pre shaped to conform to the carotid anatomy in a substantially relaxed state. Alternatively, the electrodes 302 may have a geometry and/or orientation that reduces the amount of electrode 302 strain. Optionally, as described in more detail below, the backing or base structure 306 may be elastic or stretchable to facilitate wrapping of and conforming to the carotid sinus or other vascular structure.

For example, in FIG. 6, the electrodes 302 are shown to have a serpentine or wavy shape. The serpentine shape of the electrodes 302 reduces the amount of strain seen by the electrode material when wrapped around a carotid structure. In addition, the serpentine shape of the electrodes increases the contact surface area of the electrode 302 with the carotid tissue. As an alternative, the electrodes 302 may be arranged to be substantially orthogonal to the wrap direction (i.e., substantially parallel to the axis of the carotid arteries) as shown in FIG. 7. In this alternative, the electrodes 302 each have a length and a width or diameter, wherein the length is substantially greater than the width or diameter. The electrodes 302 each have a longitudinal axis parallel to the length thereof, wherein the longitudinal axis is orthogonal to the wrap direction and substantially parallel to the longitudinal axis of the carotid artery about which the device 300 is wrapped. As with the multiple electrode embodiments described previously, the electrodes 302 may be connected to a single channel or multiple channels as discussed in more detail hereinafter.

Figure 8:
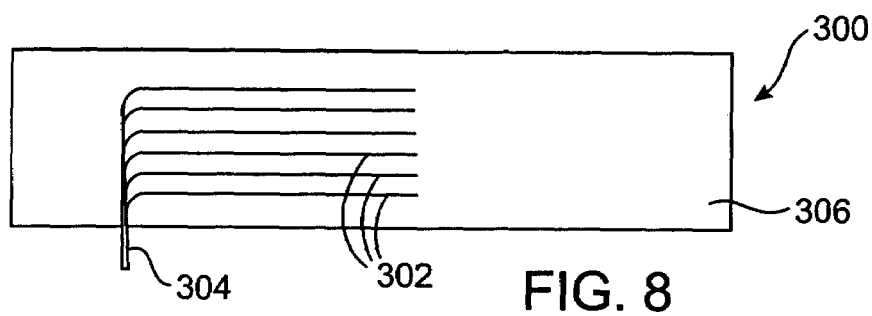
FIGS. 8-11 are schematic illustrations of various multi-channel electrodes for extravascular electrical activation embodiments.

Refer now to FIGS. 8-11 which schematically illustrate various multi-channel electrodes for the extravascular electrical activation device 300. FIG. 8 illustrates a six (6) channel electrode assembly including six (6) separate elongate electrodes 302 extending adjacent to and parallel with each other. The electrodes 302 are each connected to multi-channel cable 304. Some of the electrodes 302 may be common, thereby reducing the number of conductors necessary in the cable 304.

Base structure or substrate 306 may comprise a flexible and electrically insulating material suitable for implantation, such as silicone, perhaps reinforced with a flexible material such as polyester fabric. The base 306 may have a length suitable to wrap around all (360°) or a portion (i.e., less than 360°) of the circumference of one or more of the carotid arteries adjacent the carotid sinus 20. The electrodes 302 may extend around a portion (i.e., less than 360° such as 270°, 180° or 90°) of the circumference of one or more of the carotid arteries adjacent the carotid sinus 20. To this end, the electrodes 302 may have a length that is less than (e.g., 75%, 50% or 25%) the length of the base 206. The electrodes 302 may be parallel, orthogonal or oblique to the length of the base 306, which is generally orthogonal to the axis of the carotid artery to which it is disposed about. Preferably, the base structure or backing will be elastic (i.e., stretchable), typically being composed of at least in part of silicone, latex, or other elastomer. If such elastic structures are reinforced, the reinforcement should be arranged so that it does not interfere with the ability of the base to stretch and conform to the vascular surface.

The electrodes 302 may comprise round wire, rectangular ribbon or foil formed of an electrically conductive and radiopaque material such as platinum. The base structure 306 substantially encapsulates the electrodes 302, leaving only an exposed area for electrical connection to extravascular carotid sinus tissue. For example, each electrode 302 may be partially recessed in the base 206 and may have one side exposed along all or a portion of its length for electrical connection to carotid tissue. Electrical paths through the carotid tissues may be defined by one or more pairs of the elongate electrodes 302.

In all embodiments described with reference to FIGS. 8-11, the multi-channel electrodes 302 may be selectively activated for purposes of mapping and targeting a specific area of the carotid sinus 20 to determine the best combination of electrodes 302 (e.g., individual pair, or groups of pairs) to activate for maximum baroreceptor responsiveness, as described elsewhere herein. In addition, the multi-channel electrodes 302 may be selectively activated for purposes of reducing the exposure of tissue areas to activation to maintain long term efficacy as described, as described elsewhere herein. For these purposes, it may be useful to utilize more than two (2) electrode channels. Alternatively, the electrodes 302 may be connected to a single channel whereby baroreceptors are uniformly activated throughout the sinus 20 region.

Figure 9:
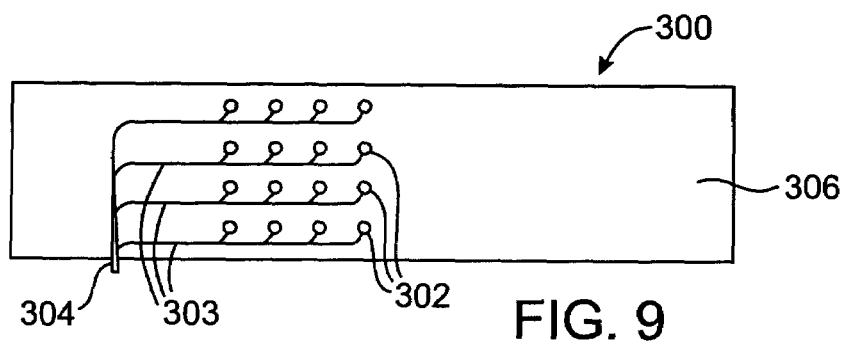

An alternative multi-channel electrode design is illustrated in FIG. 9. In this embodiment, the device 300 includes sixteen (16) individual electrode pads 302 connected to 16 channel cable 304 via 4 channel connectors 303. In this embodiment, the circular electrode pads 302 are partially encapsulated by the base structure 306 to leave one face of each button electrode 302 exposed for electrical connection to carotid tissues. With this arrangement, electrical paths through the carotid tissues may be defined by one or more pairs (bipolar) or groups (tripolar) of electrode pads 302.

Figure 10:
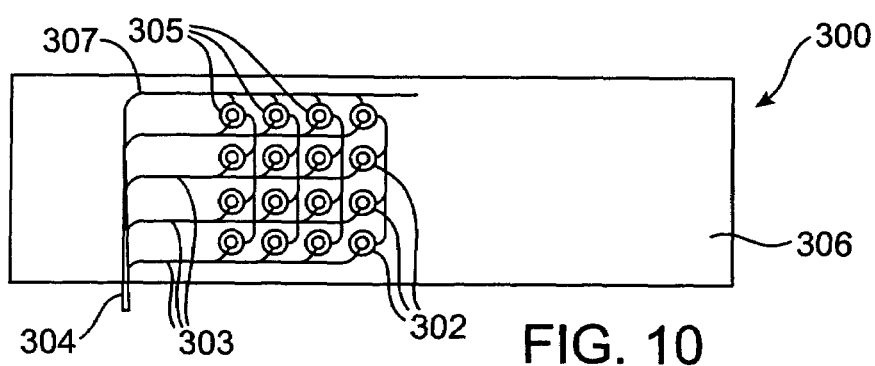

A variation of the multi-channel pad type electrode design is illustrated in FIG. 10. In this embodiment, the device 300 includes sixteen (16) individual circular pad electrodes 302 surrounded by sixteen (16) rings 305, which collectively may be referred to as concentric electrode pads 302/305. Pad electrodes 302 are connected to 17 channel cable 304 via 4 channel connectors 303, and rings 305 are commonly connected to 17 channel cable 304 via a single channel connector 307. In this embodiment, the circular shaped electrodes 302 and the rings 305 are partially encapsulated by the base structure 306 to leave one face of each pad electrode 302 and one side of each ring 305 exposed for electrical connection to carotid tissues. As an alternative, two rings 305 may surround each electrode 302, with the rings 305 being commonly connected. With these arrangements, electrical paths through the carotid tissues may be defined between one or more pad electrode 302/ring 305 sets to create localized electrical paths.

Figure 11:
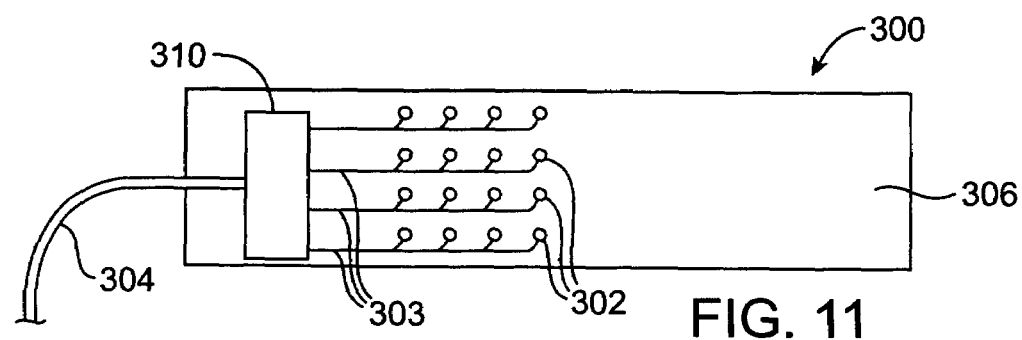

Another variation of the multi-channel pad electrode design is illustrated in FIG. 11. In this embodiment, the device 300 includes a control IC chip 310 connected to 3 channel cable 304. The control chip 310 is also connected to sixteen (16) individual pad electrodes 302 via 4 channel connectors 303. The control chip 310 permits the number of channels in cable 304 to be reduced by utilizing a coding system. The control system 60 sends a coded control signal which is received by chip 310. The chip 310 converts the code and enables or disables selected electrode 302 pairs in accordance with the code.

For example, the control signal may comprise a pulse wave form, wherein each pulse includes a different code. The code for each pulse causes the chip 310 to enable one or more pairs of electrodes, and to disable the remaining electrodes. Thus, the pulse is only transmitted to the enabled electrode pair(s) corresponding to the code sent with that pulse. Each subsequent pulse would have a different code than the preceding pulse, such that the chip 310 enables and disables a different set of electrodes 302 corresponding to the different code. Thus, virtually any number of electrode pairs may be selectively activated using control chip 310, without the need for a separate channel in cable 304 for each electrode 302. By reducing the number of channels in cable 304, the size and cost thereof may be reduced.

Optionally, the IC chip 310 may be connected to feedback sensor 80, taking advantage of the same functions as described with reference to FIG. 3. In addition, one or more of the electrodes 302 may be used as feedback sensors when not enabled for activation. For example, such a feedback sensor electrode may be used to measure or monitor electrical conduction in the vascular wall to provide data analogous to an ECG. Alternatively, such a feedback sensor electrode may be used to sense a change in impedance due to changes in blood volume during a pulse pressure to provide data indicative of heart rate, blood pressure, or other physiologic parameter.

Figure 12:
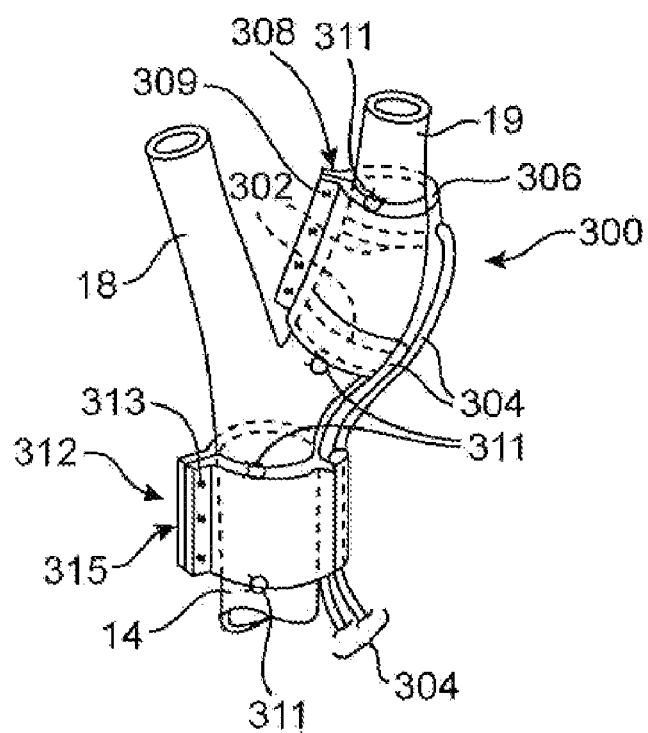
FIG. 12 is a schematic illustration of an extravascular electrical activation device including a tether and an anchor disposed about the carotid sinus and common carotid artery.

Refer now to FIG. 12 which schematically illustrates an extravascular electrical activation device 300 including a support collar or anchor 312. In this embodiment, the activation device 300 is wrapped around the internal carotid artery 19 at the carotid sinus 20, and the support collar 312 is wrapped around the common carotid artery 14. The activation device 300 is connected to the support collar 312 by cables 304, which act as a loose tether. With this arrangement, the collar 312 isolates the activation device from movements and forces transmitted by the cables 304 proximal of the support collar, such as may be encountered by movement of the control system 60 and/or driver 66. As an alternative to support collar 312, a strain relief (not shown) may be connected to the base structure 306 of the activation device 300 at the juncture between the cables 304 and the base 306. With either approach, the position of the device 300 relative to the carotid anatomy may be better maintained despite movements of other parts of the system.

In this embodiment, the base structure 306 of the activation device 300 may comprise molded tube, a tubular extrusion, or a sheet of material wrapped into a tube shape utilizing a suture flap 308 with sutures 309 as shown. The base structure 306 may be formed of a flexible and biocompatible material such as silicone, which may be reinforced with a flexible material such as polyester fabric available under the trade name DACRON® to form a composite structure. The inside diameter of the base structure 306 may correspond to the outside diameter of the carotid artery at the location of implantation, for example 6 to 8 mm. The wall thickness of the base structure 306 may be very thin to maintain flexibility and a low profile, for example less than 1 mm. If the device 300 is to be disposed about a sinus bulge 21, a correspondingly shaped bulge may be formed into the base structure for added support and assistance in positioning.

The electrodes 302 (shown in phantom) may comprise round wire, rectangular ribbon or foil, formed of an electrically conductive and radiopaque material such as platinum or platinum iridium. The electrodes may be molded into the base structure 306 or adhesively connected to the inside diameter thereof, leaving a portion of the electrode exposed for electrical connection to carotid tissues. The electrodes 302 may encompass less than the entire inside circumference (e.g., 300°) of the base structure 306 to avoid shorting. The electrodes 302 may have any of the shapes and arrangements described previously. For example, as shown in FIG. 12, two rectangular ribbon electrodes 302 may be used, each having a width of 1 mm spaced 1.5 mm apart.

The support collar 312 may be formed similarly to base structure 306. For example, the support collar may comprise molded tube, a tubular extrusion, or a sheet of material wrapped into a tube shape utilizing a suture flap 315 with sutures 313 as shown. The support collar 312 may be formed of a flexible and biocompatible material such as silicone, which may be reinforced to form a composite structure. The cables 304 are secured to the support collar 312, leaving slack in the cables 304 between the support collar 312 and the activation device 300.

In all embodiments described herein, it may be desirable to secure the activation device to the vascular wall using sutures or other fixation means. For example, sutures 311 may be used to maintain the position of the electrical activation device 300 relative to the carotid anatomy (or other vascular site containing baroreceptors). Such sutures 311 may be connected to base structure 306, and pass through all or a portion of the vascular wall. For example, the sutures 311 may be threaded through the base structure 306, through the adventitia of the vascular wall, and tied. If the base structure 306 comprises a patch or otherwise partially surrounds the carotid anatomy, the corners and/or ends of the base structure may be sutured, with additional sutures evenly distributed therebetween. In order to minimize the propagation of a hole or a tear through the base structure 306, a reinforcement material such as polyester fabric may be embedded in the silicone material. In addition to sutures, other fixation means may be employed such as staples or a biocompatible adhesive, for example.

Figure 13:
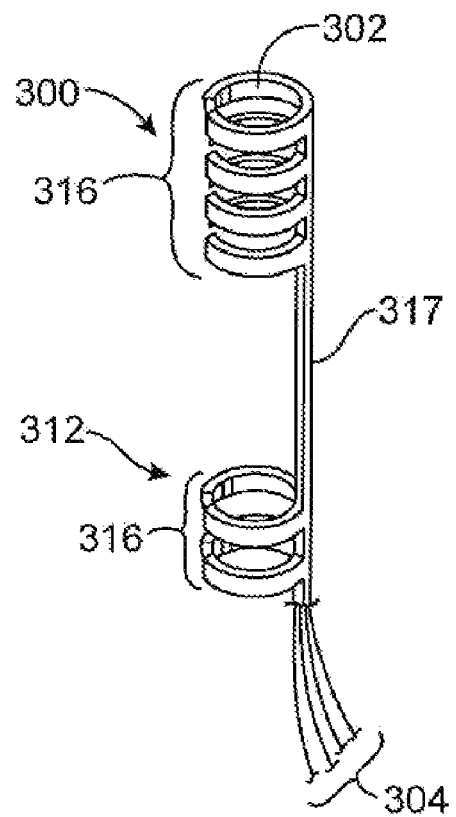
FIG. 13 is a schematic illustration of an alternative extravascular electrical activation device including a plurality of ribs and a spine.

Refer now to FIG. 13 which schematically illustrates an alternative extravascular electrical activation device 300 including one or more electrode ribs 316 interconnected by spine 317. Optionally, a support collar 312 having one or more (non electrode) ribs 316 may be used to isolate the activation device 300 from movements and forces transmitted by the cables 304 proximal of the support collar 312.

The ribs 316 of the activation device 300 are sized to fit about the carotid anatomy, such as the internal carotid artery 19 adjacent the carotid sinus 20. Similarly, the ribs 316 of the support collar 312 may be sized to fit about the carotid anatomy, such as the common carotid artery 14 proximal of the carotid sinus 20. The ribs 316 may be separated, placed on a carotid artery, and closed thereabout to secure the device 300 to the carotid anatomy.

Each of the ribs 316 of the device 300 includes an electrode 302 on the inside surface thereof for electrical connection to carotid tissues. The ribs 316 provide insulating material around the electrodes 302, leaving only an inside portion exposed to the vascular wall. The electrodes 302 are coupled to the multi-channel cable 304 through spine 317. Spine 317 also acts as a tether to ribs 316 of the support collar 312, which do not include electrodes since their function is to provide support. The multi-channel electrode 302 functions discussed with reference to FIGS. 8-11 are equally applicable to this embodiment.

The ends of the ribs 316 may be connected (e.g., sutured) after being disposed about a carotid artery, or may remain open as shown. If the ends remain open, the ribs 316 may be formed of a relatively stiff material to ensure a mechanical lock around the carotid artery. For example, the ribs 316 may be formed of polyethylene, polypropylene, PTFE, or other similar insulating and biocompatible material. Alternatively, the ribs 316 may be formed of a metal such as stainless steel or a nickel titanium alloy, as long as the metallic material was electrically isolated from the electrodes 302. As a further alternative, the ribs 316 may comprise an insulating and biocompatible polymeric material with the structural integrity provided by metallic (e.g., stainless steel, nickel titanium alloy, etc.) reinforcement. In this latter alternative, the electrodes 302 may comprise the metallic reinforcement.

Figure 14:
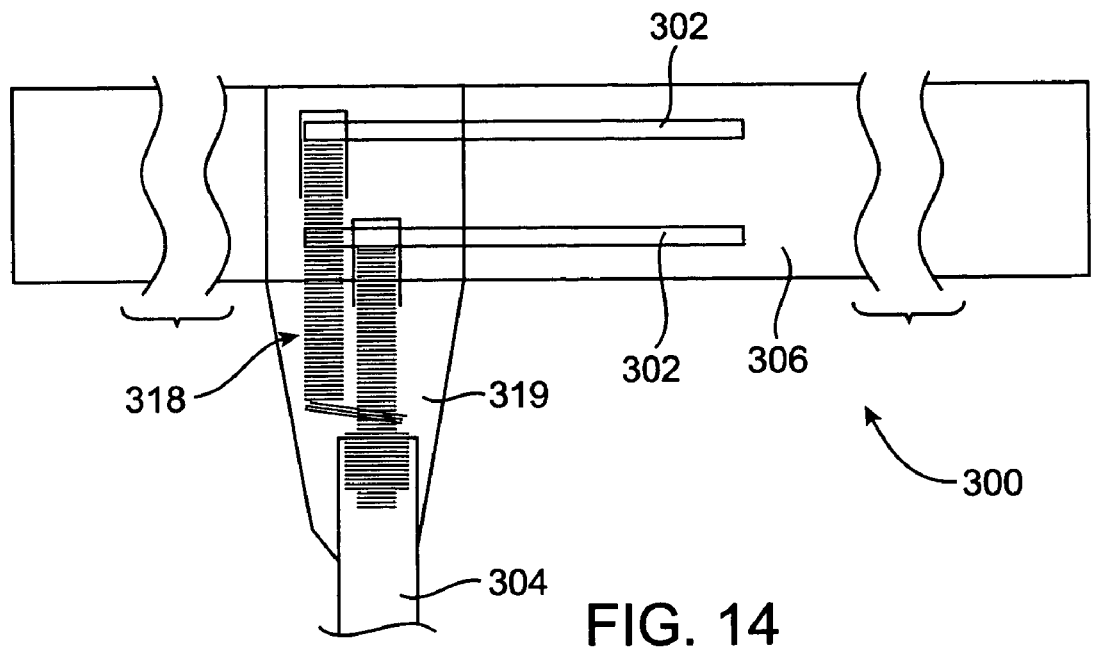
FIG. 14 is a schematic illustration of an electrode assembly for extravascular electrical activation embodiments.

Refer now to FIG. 14 which schematically illustrates a specific example of an electrode assembly for an extravascular electrical activation device 300. In this specific example, the base structure 306 comprises a silicone sheet having a length of 5.0 inches, a thickness of 0.007 inches, and a width of 0.312 inches. The electrodes 302 comprise platinum ribbon having a length of 0.47 inches, a thickness of 0.0005 inches, and a width of 0.040 inches. The electrodes 302 are adhesively connected to one side of the silicone sheet 306.

The electrodes 302 are connected to a modified bipolar endocardial pacing lead, available under the trade name CONIFIX from Innomedica (now BIOMEC Cardiovascular, Inc.), model number 501112. The proximal end of the cable 304 is connected to the control system 60 or driver 66 as described previously. The pacing lead is modified by removing the pacing electrode to form the cable body 304. The MP35 wires are extracted from the distal end thereof to form two coils 318 positioned side by side having a diameter of about 0.020 inches. The coils 318 are then attached to the electrodes utilizing 316 type stainless steel crimp terminals laser welded to one end of the platinum electrodes 302. The distal end of the cable 304 and the connection between the coils 318 and the ends of the electrodes 302 are encapsulated by silicone.

Figure 15:
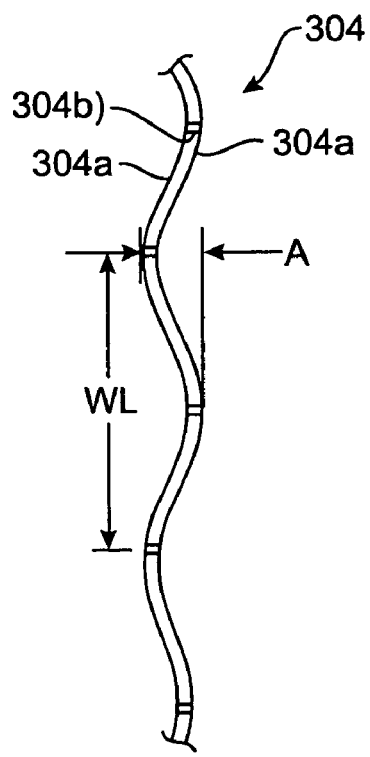
FIG. 15 is a schematic illustration of a fragment of an alternative cable for use with an electrode assembly such as shown in FIG. 14.

The cable 304 illustrated in FIG. 14 comprises a coaxial type cable including two coaxially disposed coil leads separated into two separate coils 318 for attachment to the electrodes 302. An alternative cable 304 construction is illustrated in FIG. 15. FIG. 15 illustrates an alternative cable body 304 which may be formed in a curvilinear shape such as a sinusoidal configuration, prior to implantation. The curvilinear configuration readily accommodates a change in distance between the device 300 and the control system 60 or the driver 66. Such a change in distance may be encountered during flexion and/or extension of the neck of the patient after implantation.

In this alternative embodiment, the cable body 304 may comprise two or more conductive wires 304a arranged coaxially or collinearly as shown. Each conductive wire 304a may comprise a multifilament structure of suitable conductive material such as stainless steel or MP35N. An insulating material may surround the wire conductors 304a individually and/or collectively. For purposes of illustration only, a pair of electrically conductive wires 304a having an insulating material surrounding each wire 304a individually is shown. The insulated wires 304a may be connected by a spacer 304b comprising, for example, an insulating material. An additional jacket of suitable insulating material may surround each of the conductors 304a. The insulating jacket may be formed to have the same curvilinear shape of the insulated wires 304a to help maintain the shape of the cable body 304 during implantation.

If a sinusoidal configuration is chosen for the curvilinear shape, the amplitude (A) may range from 1 mm to 10 mm, and preferably ranges from 2 mm to 3 mm. The wavelength (WL) of the sinusoid may range from 2 mm to 20 mm, and preferably ranges from 4 mm to 10 mm. The curvilinear or sinusoidal shape may be formed by a heat setting procedure utilizing a fixture which holds the cable 304 in the desired shape while the cable is exposed to heat. Sufficient heat is used to heat set the conductive wires 304a and/or the surrounding insulating material. After cooling, the cable 304 may be removed from the fixture, and the cable 304 retains the desired shape.

Figure 16:
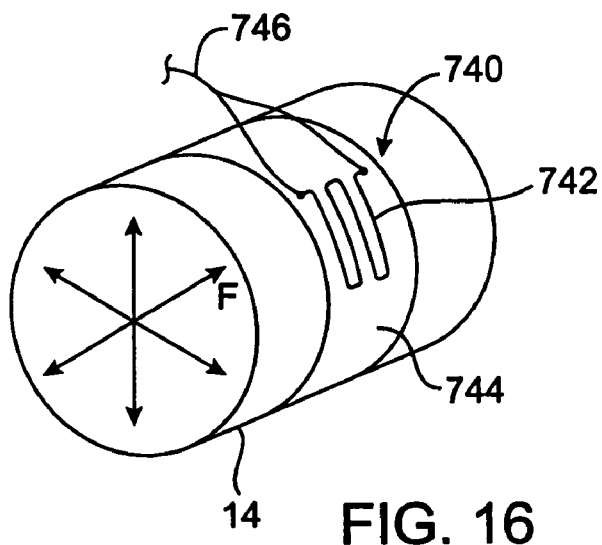
FIG. 16 illustrates a foil strain gauge for measuring expansion force of a carotid artery or other blood vessel.
Figure 17:
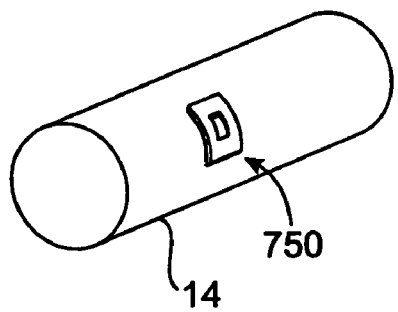
FIG. 17 illustrates a transducer which is adhesively connected to the wall of an artery.
Figure 18:
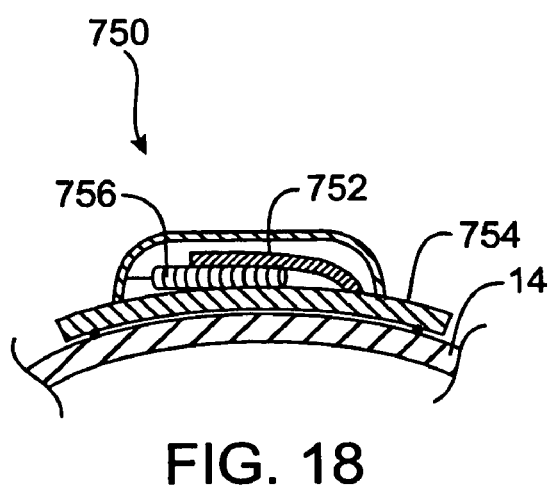
FIG. 18 is a cross-sectional view of the transducer of FIG. 17.

Refer now to FIGS. 16-18 which illustrate various transducers that may be mounted to the wall of a vessel such as a carotid artery 14 to monitor wall expansion or contraction using strain, force and/or pressure gauges. An example of an implantable blood pressure measurement device that may be disposed about a blood vessel is disclosed in U.S. Pat. No. 6,106,477 to Miesel et al., the entire disclosure of which is incorporated herein by reference. The output from such gauges may be correlated to blood pressure and/or heart rate, for example, and may be used to provide feedback to the control system 60 as described previously herein. In FIG. 16, an implantable pressure measuring assembly comprises a foil strain gauge or force sensing resistor device 740 disposed about an artery such as common carotid artery 14. A transducer portion 742 may be mounted to a silicone base or backing 744 which is wrapped around and sutured or otherwise attached to the artery 14.

Alternatively, the transducer 750 may be adhesively connected to the wall of the artery 14 using a biologically compatible adhesive such as cyanoacrylate as shown in FIG. 17. In this embodiment, the transducer 750 comprises a micro machined sensor (MEMS) that measures force or pressure. The MEMS transducer 750 includes a micro arm 752 (shown in section in FIG. 18) coupled to a silicon force sensor contained over an elastic base 754. A cap 756 covers the arm 752 a top portion of the base 754. The base 754 include an interior opening creating access from the vessel wall 14 to the arm 752. An incompressible gel 756 fills the space between the arm 752 and the vessel wall 14 such that force is transmitted to the arm upon expansion and contraction of the vessel wall. In both cases, changes in blood pressure within the artery cause changes in vessel wall stress which are detected by the transducer and which may be correlated with the blood pressure.

Figure 19:
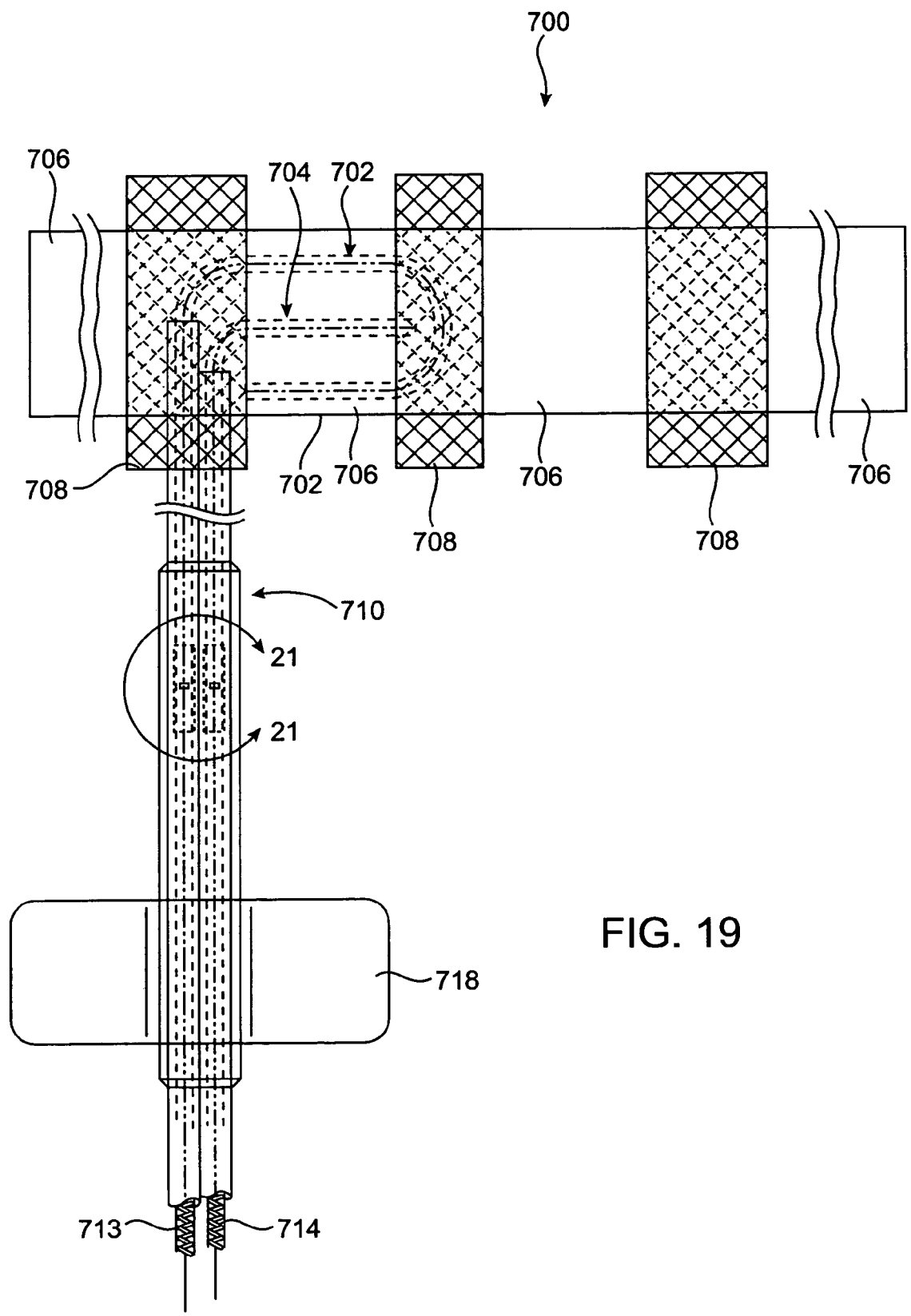
FIG. 19 illustrates a first exemplary electrode assembly having an elastic base and plurality of attachment tabs.
Figure 20:
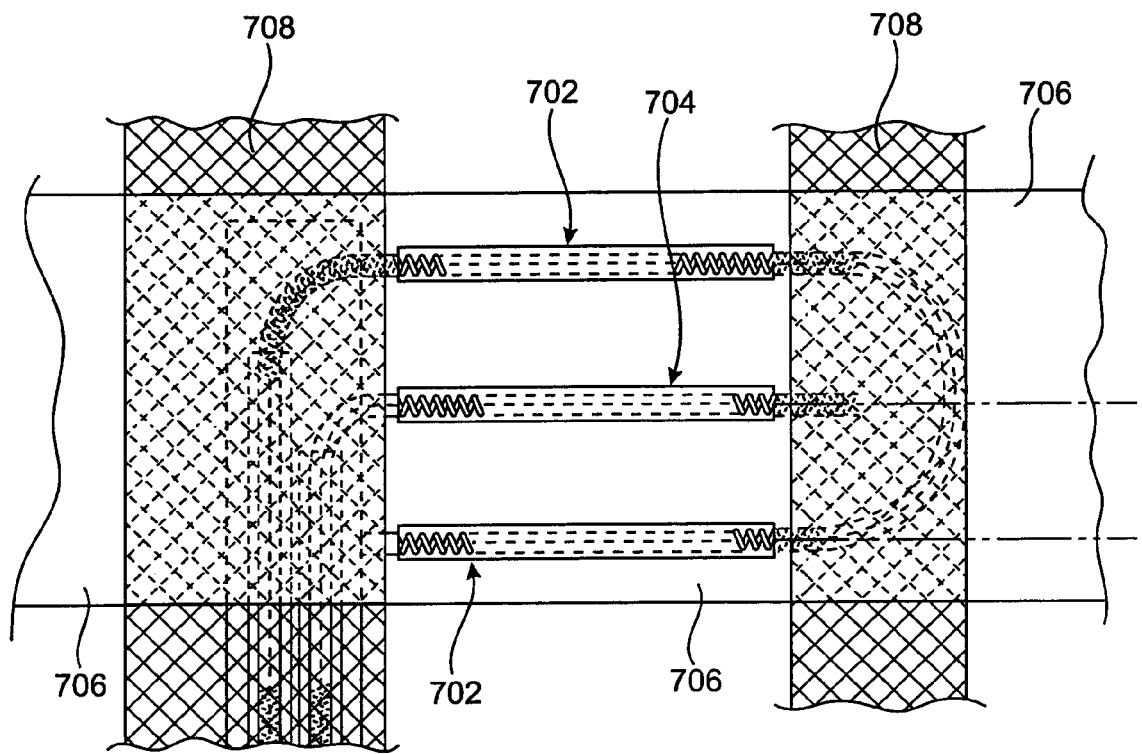
FIG. 20 is a more detailed illustration of the electrode-carrying surface of the electrode assembly of FIG. 19.
Figure 21:
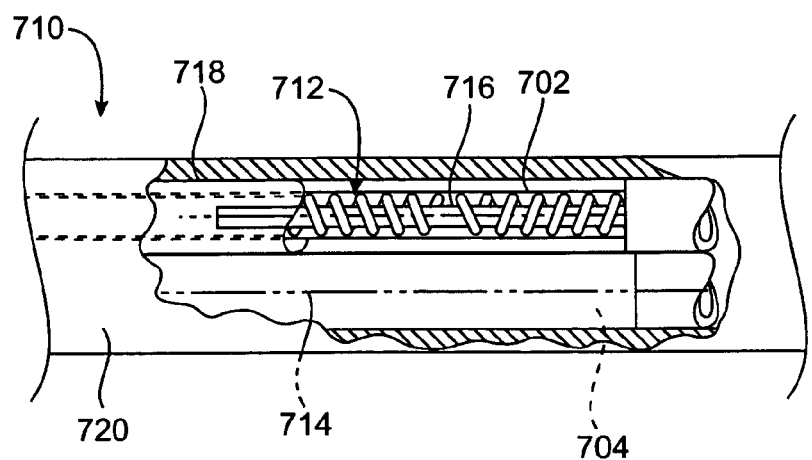
FIG. 21 is a detailed illustration of electrode coils which are present in an elongate lead of the electrode assembly of FIG. 19.

Refer now to FIGS. 19-21 which illustrate an alternative extravascular electrical activation device 700, which, may also be referred to as an electrode cuff device or more generally as an "electrode assembly." Except as described herein and shown in the drawings, device 700 may be the same in design and function as extravascular electrical activation device 300 described previously.

As seen in FIGS. 19 and 20, electrode assembly or cuff device 700 includes coiled electrode conductors 702/704 embedded in a flexible support 706. In the embodiment shown, an outer electrode coil 702 and an inner electrode coil 704 are used to provide a pseudo tripolar arrangement, but other polar arrangements are applicable as well as described previously. The coiled electrodes 702/704 may be formed of fine round, flat or ellipsoidal wire such as 0.002 inch diameter round PtIr alloy wire wound into a coil form having a nominal diameter of 0.015 inches with a pitch of 0.004 inches, for example. The flexible support or base 706 may be formed of a biocompatible and flexible (preferably elastic) material such as silicone or other suitable thin walled elastomeric material having a wall thickness of 0.005 inches and a length (e.g., 2.95 inches) sufficient to surround the carotid sinus, for example.

Each turn of the coil in the contact area of the electrodes 702/704 is exposed from the flexible support 706 and any adhesive to form a conductive path to the artery wall. The exposed electrodes 702/704 may have a length (e.g., 0.236 inches) sufficient to extend around at least a portion of the carotid sinus, for example. The electrode cuff 700 is assembled flat with the contact surfaces of the coil electrodes 702/704 tangent to the inside plane of the flexible support 706. When the electrode cuff 700 is wrapped around the artery, the inside contact surfaces of the coiled electrodes 702/704 are naturally forced to extend slightly above the adjacent surface of the flexible support, thereby improving contact to the artery wall.

The ratio of the diameter of the coiled electrodes 702/704 to the wire diameter is preferably large enough to allow the coil to bend and elongate without significant bending stress or torsional stress in the wire. Flexibility is a significant advantage of this design which allows the electrode cuff 700 to conform to the shape of the carotid artery and sinus, and permits expansion and contraction of the artery or sinus without encountering significant stress or fatigue. In particular, the flexible electrode cuff 700 may be wrapped around and stretched to conform to the shape of the carotid sinus and artery during implantation. This may be achieved without collapsing or distorting the shape of the artery and carotid sinus due to the compliance of the electrode cuff 700. The flexible support 706 is able to flex and stretch with the conductor coils 702/704 because of the absence of fabric reinforcement in the electrode contact portion of the cuff 700. By conforming to the artery shape, and by the edge of the flexible support 706 sealing against the artery wall, the amount of stray electrical field and extraneous stimulation will likely be reduced.

The pitch of the coil electrodes 702/704 may be greater than the wire diameter in order to provide a space between each turn of the wire to thereby permit bending without necessarily requiring axial elongation thereof. For example, the pitch of the contact coils 702/704 may be 0.004 inches per turn with a 0.002 inch diameter wire, which allows for a 0.002 inch space between the wires in each turn. The inside of the coil may be filled with a flexible adhesive material such as silicone adhesive which may fill the spaces between adjacent wire turns. By filling the small spaces between the adjacent coil turns, the chance of pinching tissue between coil turns is minimized thereby avoiding abrasion to the artery wall. Thus, the embedded coil electrodes 702/704 are mechanically captured and chemically bonded into the flexible support 706. In the unlikely event that a coil electrode 702/704 comes loose from the support 706, the diameter of the coil is large enough to be atraumatic to the artery wall. Preferably, the centerline of the coil electrodes 702/704 lie near the neutral axis of electrode cuff structure 700 and the flexible support 706 comprises a material with isotropic elasticity such as silicone in order to minimize the shear forces on the adhesive bonds between the coil electrodes 702/704 and the support 706.

The electrode coils 702/704 are connected to corresponding conductive coils 712/714, respectively, in an elongate lead 710 which is connected to the control system 60. Anchoring wings 718 may be provided on the lead 710 to tether the lead 710 to adjacent tissue and minimize the effects or relative movement between the lead 710 and the electrode cuff 700. As seen in FIG. 21, the conductive coils 712/714 may be formed of 0.003 MP35N bifilar wires wound into 0.018 inch diameter coils which are electrically connected to electrode coils 702/704 by splice wires 716. The conductive coils 712/714 may be individually covered by an insulating covering 718 such as silicone tubing and collectively covered by insulating covering 720.

The conductive material of the electrodes 702/704 may be a metal as described above or a conductive polymer such as a silicone material filled with metallic particles such as Pt particles. In this latter embodiment, the polymeric electrodes may be integrally formed with the flexible support 706 with the electrode contacts comprising raised areas on the inside surface of the flexible support 706 electrically coupled to the lead 710 by wires or wire coils. The use of polymeric electrodes may be applied to other electrode design embodiments described elsewhere herein.

Reinforcement patches 708 such as DACRON® fabric may be selectively incorporated into the flexible support 706. For example, reinforcement patches 708 may be incorporated into the ends or other areas of the flexible support 706 to accommodate suture anchors. The reinforcement patches 708 provide points where the electrode cuff 700 may be sutured to the vessel wall and may also provide tissue in growth to further anchor the device 700 to the exterior of the vessel wall. For example, the fabric reinforcement patches 708 may extend beyond the edge of the flexible support 706 so that tissue in growth may help anchor the electrode assembly or cuff 700 to the vessel wall and may reduce reliance on the sutures to retain the electrode assembly 700 in place. As a substitute for or in addition to the sutures and tissue in growth, bioadhesives such as cyanoacrylate may be employed to secure the device 700 to the vessel wall. In addition, an adhesive incorporating conductive particles such as Pt coated micro spheres may be applied to the exposed inside surfaces of the electrodes 702/704 to enhance electrical conduction to the tissue and possibly limit conduction along one axis to limit extraneous tissue stimulation.

The reinforcement patches 708 may also be incorporated into the flexible support 706 for strain relief purposes and to help retain the coils 702/704 to the support 706 where the leads 710 attach to the electrode assembly 700 as well as where the outer coil 702 loops back around the inner coil 704. Preferably, the patches 708 are selectively incorporated into the flexible support 706 to permit expansion and contraction of the device 700, particularly in the area of the electrodes 702/704. In particular, the flexible support 706 is only fabric reinforced in selected areas thereby maintaining the ability of the electrode cuff 700 to stretch.

Referring now to FIGS. 22-26, the electrode assembly of FIGS. 19-21 can be modified to have "flattened" coil electrodes in the region of the assembly where the electrodes contact the extravascular tissue. As shown in FIG. 22, an electrode-carrying surface 801 of the electrode assembly, is located generally between parallel reinforcement strips or tabs 808. The flattened coil section 810 will generally be exposed on a lower surface 803 of the base 806 (FIG. 23) and will be covered or encapsulated by a parylene or other polymeric structure or material 802 over an upper surface 805 thereof. The coil is formed with a generally circular periphery 809, as best seen in FIGS. 24 and 26, and may be mechanically flattened, typically over a silicone or other supporting insert 815, as best seen in FIG. 25. The use of the flattened coil structure is particularly beneficial since it retains flexibility, allowing the electrodes to bend, stretch, and flex together with the elastomeric base 806, while also increasing the flat electrode area available to contact the extravascular surface.

Referring now to FIGS. 27-30, an additional electrode assembly 900 constructed in accordance with the principles of the present invention will be described. Electrode assembly 900 comprises an electrode base, typically an elastic base 902, typically formed from silicone or other elastomeric material, having an electrode-carrying surface 904 and a plurality of attachment tabs 906 (906a, 906b, 906c, and 906d) extending from the electrode-carrying surface. The attachment tabs 906 are preferably formed from the same material as the electrode-carrying surface 904 of the base 902, but could be formed from other elastomeric materials as well. In the latter case, the base will be molded, stretched or otherwise assembled from the various pieces. In the illustrated embodiment, the attachment tabs 906 are formed integrally with the remainder of the base 902, i.e., typically being cut from a single sheet of the elastomeric material.

Figure 27:
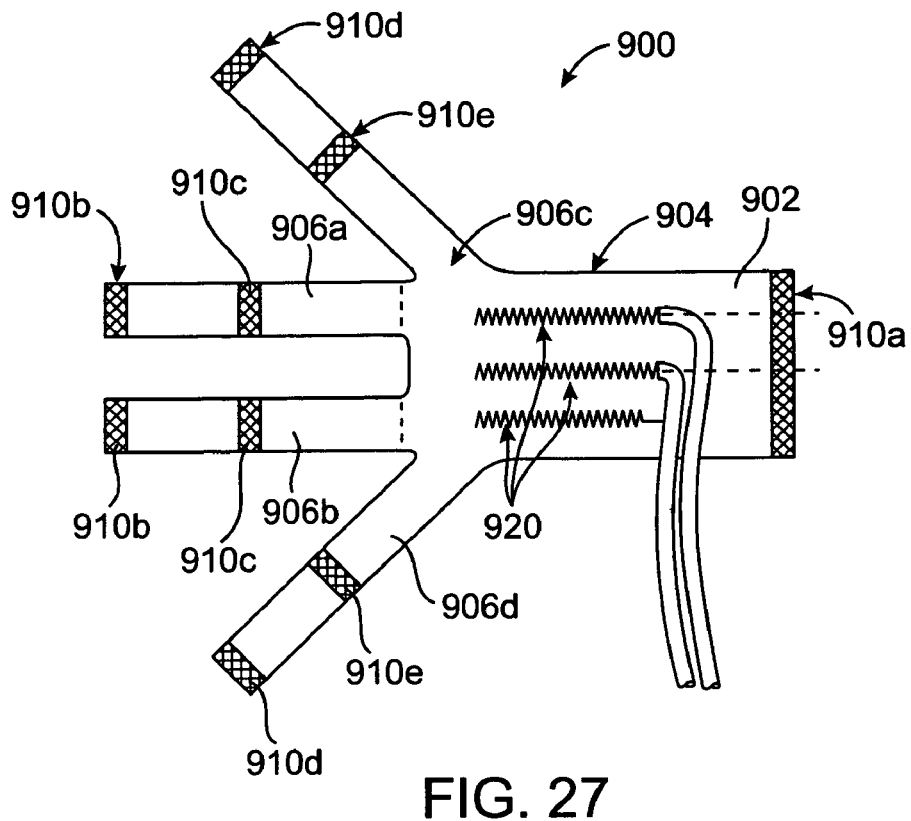
FIG. 27 is an illustration of a further exemplary electrode assembly constructed in accordance with the principles of the present invention.

The geometry of the electrode assembly 900, and in particular the geometry of the base 902, is selected to permit a number of different attachment modes to the blood vessel. In particular, the geometry of the assembly 902 of FIG. 27 is intended to permit attachment to various locations on the carotid arteries at or near the carotid sinus and carotid bifurcation.

A number of reinforcement regions 910 (910a, 910b, 910c, 910d, and 910e) are attached to different locations on the base 902 to permit suturing, clipping, stapling, or other fastening of the attachment tabs 906 to each other and/or the electrode-carrying surface 904 of the base 902. In the preferred embodiment intended for attachment at or around the carotid sinus, a first reinforcement strip 910a is provided over an end of the base 902 opposite to the end which carries the attachment tabs. Pairs of reinforcement strips 910b and 910c are provided on each of the axially aligned attachment tabs 906a and 906b (the axis runs horizontally across FIG. 27), while similar pairs of reinforcement strips 910d and 910e are provided on each of the transversely angled attachment tabs 906c and 906d. As illustrated, the tabs 906c and 906d are acutely angled relative to the axis of the base when the base is in an unstressed (unstretched) configuration prior to placement around the carotid sinus or other blood vessel, as illustrated in FIG. 27. In the illustrated embodiment, all attachment tubes will be provided on one side of the base, preferably emanating from adjacent corners of the rectangular electrode-carrying surface 904.

The structure of electrode assembly 900 permits the surgeon to implant the electrode assembly so that the electrodes 920 (which are preferably stretchable, flat-coil electrodes as described in detail above), are located at a preferred location relative to the target baroreceptors. The preferred location may be determined, for example, as described in copending application Ser. No. 09/963,991, filed on Sep. 26, 2001, the full disclosure of which incorporated herein by reference.

Figure 28:
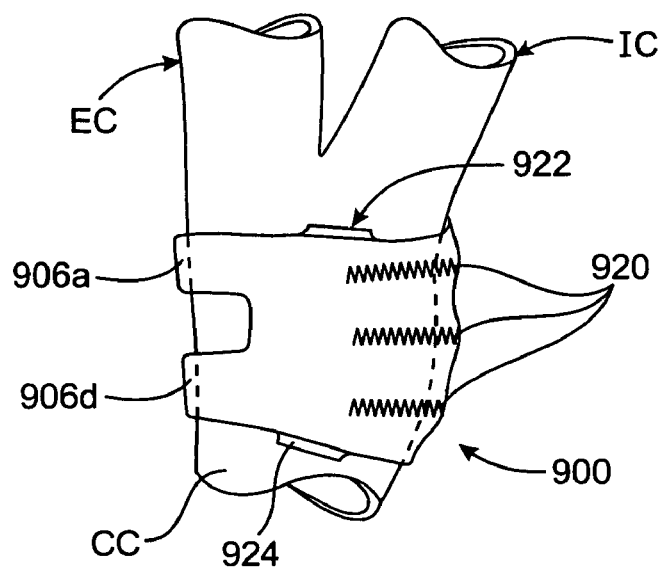
FIG. 28 illustrates the electrode assembly of FIG. 27 wrapped around the common carotid artery near the carotid bifurcation.
Figure 29:
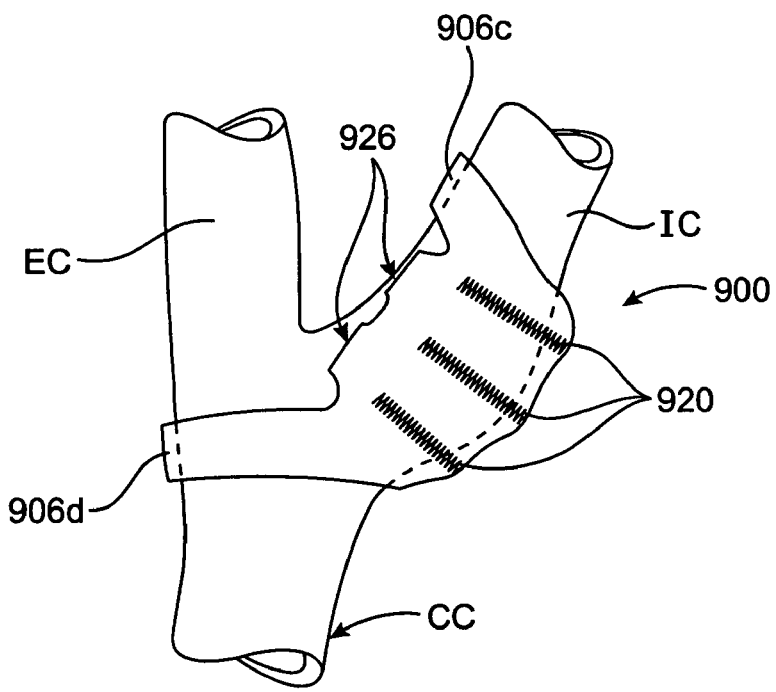
FIG. 29 illustrates the electrode assembly of FIG. 27 wrapped around the internal carotid artery.
Figure 30:
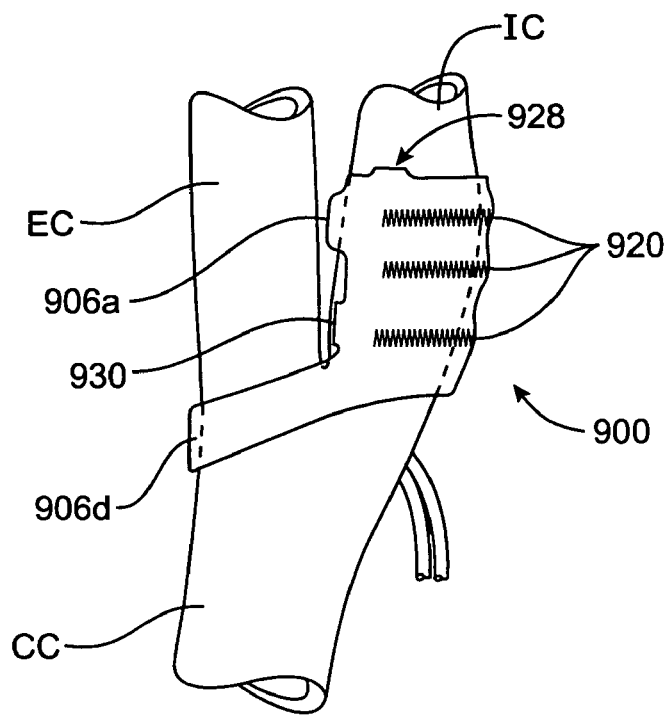
FIG. 30 is similar to FIG. 29, but with the carotid bifurcation having a different geometry.

Once the preferred location for the electrodes 920 of the electrode assembly 900 is determined, the surgeon may position the base 902 so that the electrodes 920 are located appropriately relative to the underlying baroreceptors. Thus, the electrodes 920 may be positioned over the common carotid artery CC as shown in FIG. 28, or over the internal carotid artery IC, as shown in FIGS. 29 and 30. In FIG. 28, the assembly 900 may be attached by stretching the base 902 and attachment tabs 906a and 906b over the exterior of the common carotid artery. The reinforcement tabs 906a or 906b may then be secured to the reinforcement strip 910a, either by suturing, stapling, fastening, gluing, welding, or other well-known means. Usually, the reinforcement tabs 906c and 906d will be cut off at their bases, as shown at 922 and 924, respectively.

In other cases, the bulge of the carotid sinus and the baroreceptors may be located differently with respect to the carotid bifurcation. For example, as shown in FIG. 29, the receptors may be located further up the internal carotid artery IC so that the placement of electrode assembly 900 as shown in FIG. 28 will not work. The assembly 900, however, may still be successfully attached by utilizing the transversely angled attachment tabs 906c and 906d rather than the central or axial tabs 906a and 906b. As shown in FIG. 29, the lower tab 906d is wrapped around the common carotid artery CC, while the upper attachment tab 906c is wrapped around the internal carotid artery IC. The axial attachment tabs 906a and 906b will usually be cut off (at locations 926), although neither of them could in some instances also be wrapped around the internal carotid artery IC. Again, the tabs which are used may be stretched and attached to reinforcement strip 910a, as generally described above.

Referring to FIG. 30, in instances where the carotid bifurcation has less of an angle, the assembly 900 may be attached using the upper axial attachment tab 906a and be lower transversely angled attachment tab 906d. Attachment tabs 906b and 906c may be cut off, as shown at locations 928 and 930, respectively. In all instances, the elastic nature of the base 902 and the stretchable nature of the electrodes 920 permit the desired conformance and secure mounting of the electrode assembly over the carotid sinus. It would be appreciated that these or similar structures would also be useful for mounting electrode structures at other locations in the vascular system.

In most activation device embodiments described herein, it may be desirable to incorporate anti-inflammatory agents (e.g., steroid eluting electrodes) such as described in U.S. Pat. No. 4,711,251 to Stokes, U.S. Pat. No. 5,522,874 to Gates and U.S. Pat. No. 4,972,848 to Di Domenico et al., the entire disclosures of which are incorporated herein by reference. Such agents reduce tissue inflammation at the chronic interface between the device (e.g., electrodes) and the vascular wall tissue, to thereby increase the efficiency of stimulus transfer, reduce power consumption, and maintain activation efficiency, for example.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A device for mounting over a circumference of a carotid sinus of a patient, the device comprising:
   a base having first and second ends, a longitudinal axis therebetween, and an axial length sufficient to extend around the circumference of the carotid sinus, wherein said base is sufficiently elastic to conform to said circumference as the carotid sinus changes in shape and size with heart pulse;
   an axial attachment tab extending in the axial direction from an end of the base;

a transversely angled attachment tab extending transversely from an end of the base at an acute angle relative to the longitudinal axis of the base when the base is in an unstressed configuration prior to placement about the carotid sinus; and one or more elongate electrodes connected to the base;

wherein either or both of the axial attachment tab and the transversely angled attachment tab may be wrapped around the carotid sinus or the internal carotid artery and attached to the base or blood vessel to accommodate the shape of the carotid sinus.

2. A device as in claim 1, comprising two or more electrodes positioned circumferentially and adjacent each other on the base.

3. A device as in claim 1, wherein the electrodes extend less than 75% of the length of the base.

4. A device as in claim 1, wherein the electrodes extend less than 50% of the length of the base.

5. A device as in claim 1, wherein the electrodes extend less than 25% of the length of the base.

6. A device as in claim 1, wherein the elastic base comprises an elastomeric sheet.

7. A device as in claim 6, wherein the elastomeric sheet comprises an elastomer selected from the group consisting of silicone, polyurethane, and latex.

8. A device as in claim 1, further comprising a pair of axial attachment tabs and a pair of transversely angled attachment tabs, wherein both of the transversely angled attachment tabs extend from the base at acute angles relative to the exis of the base and wherein one axial and one transversely angled attachment tab are attached at one corner of one end and another axial and another transversely angled attachment tab are attached at the other corner of the one end.

9. A device as in claim 1, wherein the electrodes comprise coils in which the individual turns of the coil are flattened in a plane parallel to that of the elastic base.

10. An extravascular electrode assembly comprising:

a base adapted to be attached over the outside of a blood vessel, said base having an electrode-carrying surface and at least four attachment tabs extending away from the electrode-carrying surface, wherein the base has a longitudinal axis and is sufficiently elastic to conform to a circumference of a blood vessel and wherein at least two tabs are axially aligned with the longitudinal axis of the base and at least two tabs are angled acutely relative to the longitudinal axis when the base is in an unstressed configuration prior to placement around the blood vessel to permit selective ones of the tabs to be wrapped around the blood vessel while others of the tabs are removed; and an electrode structure on the electrode-carrying surface.

11. An electrode assembly as in claim 10, wherein the electrode-carrying surface is rectangular and the at least two axially aligned tabs extend from adjacent corners of the surface, wherein the two acutely transversely angled tabs extend from the same corners.

12. An electrode assembly as in claim 10, wherein individual turns of the elongate coil electrode are flattened in a plane parallel to that of the elastic backing.

13. An electrode assembly as in claim 10, wherein the elastic base comprises an elastomeric sheet.

14. An electrode assembly as in claim 13, wherein the elastomeric sheet comprise an elastomer selected from the group consisting of silicone, polyurethane, and latex.

15. An electrode assembly as in claim 10, comprising two or more electrodes positioned circumferentially and adjacent each other on the base.

16. An electrode assembly as in claim 10, wherein the electrodes extend less than 75% of the length of the base.

17. An electrode assembly as in claim 10, wherein the electrodes extend less than 50% of the length of the base.

18. An electrode assembly as in claim 10, wherein the electrodes extend less than 25% of the length of the base.

19. An electrode assembly as in claim 10, wherein the base has first and second ends, and wherein the ends are adapted to be joined.

20. A method for wrapping an electrode assembly over carotid sinus, said method comprising:

providing an electrode assembly comprising an elastic base having a longitudinal axis, a plurality of attachment tabs including at least two tabs aligned axially with the longitudinal axis of the base and two tabs attached to the base at an acute angle relative to the longitudinal axis, and at least one electrode sufficiently stretchable to stretch with expansions and contractions of the the carotid sinus with heart pulse secured over a surface of the elastic base;

conforming the base over an exterior of the carotid sinus, wherein at least a portion of the electrode assembly can flex and stretch with expansions and contractions of the carotid sinus with heart pulse; and securing ends of the elastic base together and!or to the vessel wall to hold the electrode assembly in place, wherein securing said ends includes wrapping at least two one of said plurality of tabs around the carotid sinus and cutting off the remaining tabs which are not wrapped around the carotid sinus.

21. A method as in claim 20, wherein conforming comprises locating the at least one electrode over a target site in the carotid sinus.

22. A method as in claim 21, wherein the target site comprises excitable tissue.

23. A method as in claim 22, wherein the excitable tissue comprises baroreceptors in a wall of the the carotid sinus.

24. A method as in claim 20, wherein conforming the base comprises covering a circumferential distance around the the carotid sinus equal to at least 25% of the circumference of the blood vessel exterior.

25. A method as in claim 24, wherein conforming the base comprises covering a circumferential distance around the the carotid sinus equal to at least 50% of the circumference of the the carotid sinus exterior.

26. A method as in claim 24, wherein conforming the base comprises covering a circumferential distance around the the carotid sinus equal to at least 66% of the circumference of the blood vessel exterior.

27. A method as in claim 24, wherein conforming the base comprises covering a circumferential distance around the the carotid sinus equal to at least 75% of the circumference of the the carotid sinus exterior.

28. A method as in claim 24, wherein the base is conformed over the entire circumference of the the carotid sinus exterior.

29. A method as in claim 20, further comprising wrapping at least one tab around an internal carotid artery.

30. A method as in claim 29, wherein at least one axially aligned tab is wrapped around the common carotid artery and at least one acutely transversely angled tab is wrapped around the internal carotid artery.

* * * * *